United States Patent
Kurane et al.

(10) Patent No.: US 6,495,326 B2
(45) Date of Patent: Dec. 17, 2002

(54) METHOD FOR DETERMINING A CONCENTRATION OF TARGET NUCLEIC ACID MOLECULES, NUCLEIC ACID PROBES FOR THE METHOD, AND METHOD FOR ANALYZING DATA OBTAINED BY THE METHOD

(75) Inventors: Ryuichiro Kurane, Tukuba (JP); Takahiro Kanagawa, Tukuba (JP); Yoichi Kamagata, Tukuba (JP); Shinya Kurata, Tokyo (JP); Kazutaka Yamada, Tokyo (JP); Toyokazu Yokomaku, Tokyo (JP); Osamu Koyama, Tokyo (JP); Kenta Furusho, Tokyo (JP)

(73) Assignees: Japan Bioindustry Association, Tokyo (JP); Secretary of Agency of Industrial Science and Technology, Tokyo (JP); Kankyo Engineering Co., Ltd., Tokyo (JP)

( * ) Notice: Subject to any disclaimer, the term of this patent is extended or adjusted under 35 U.S.C. 154(b) by 0 days.

(21) Appl. No.: 09/725,256

(22) Filed: Nov. 29, 2000

(65) Prior Publication Data

US 2001/0000148 A1 Apr. 5, 2001

Related U.S. Application Data

(62) Division of application No. 09/556,127, filed on Apr. 20, 2000.

(30) Foreign Application Priority Data

Apr. 20, 1999 (JP) .......................................... 11-111601

(51) Int. Cl.[7] .......................... C12Q 1/68; C12P 19/34; C07H 21/02
(52) U.S. Cl. ...................... 435/6; 435/91.1; 435/91.2; 536/23.1; 536/24.3; 536/24.31; 536/24.33; 702/19; 702/20
(58) Field of Search .................. 435/6, 91.2, 91.1; 536/231, 24.3, 24.31, 24.33; 702/19.2

(56) References Cited

U.S. PATENT DOCUMENTS

| | | | | |
|---|---|---|---|---|
| 5,538,848 A | * | 7/1996 | Livak et al. ................... | 435/5 |
| 5,712,125 A | * | 1/1998 | Uhlen ....................... | 435/91.2 |
| 5,753,444 A | | 5/1998 | Wu et al. ...................... | 435/6 |
| 5,766,889 A | | 6/1998 | Atwood ..................... | 435/91.2 |
| 6,174,670 B1 | * | 1/2001 | Wittwer et al. ................ | 435/6 |

OTHER PUBLICATIONS

Morrison et al, "Solution phase detection of polynucleotides using interacting fluorescent labels and competitive hybridization", Anal. Biochem. (1989) 183:231–244.*

Yguerabide et al, "Quantitative fluorescence method for continuous measurement of DNA hybridization kinetics using a fluorescent intercalator" Anal. Biochem. 228:208–220 (1995).*

* cited by examiner

*Primary Examiner*—Jeffrey Fredman
(74) *Attorney, Agent, or Firm*—Oblon, Spivak, McClelland, Maier & Neustadt, P.C.

(57) ABSTRACT

A method is provided for determining a concentration of a target nucleic acid by using a nucleic acid probe labeled with a fluorescent dye. The method comprises:
  providing, as the probe, a nucleic acid probe capable of reducing fluorescence emission from the fluorescent dye when hybridized with the target nucleic acid;
  hybridizing the probe to the target nucleic acid; and
  measuring a decrease in fluorescence emission from the fluorescent dye after the hybridization relative to fluorescence emission from the fluorescent dye before the hybridization.

48 Claims, 14 Drawing Sheets

A : 35 − nucleotides − chained deoxyriboligonucleic acid probe
B : 35 − nucleotides − chained 2 − O − Me probe
C : 17 − nucleotides − chained deoxyriboligonucleic acid probe
D : 17 − nucleotides − chained 2 − O − Me probe HP : Helper probe HP + (M) : Helper probe + 2 − O − Me probe HP + (D) : Helper probe + deoxyribooligonucleotide probe Ref. : Reference C : Cytosine, G : Guanine

METHOD FOR DETERMINING A CONCENTRATION OF TARGET NUCLEIC ACID MOLECULES, NUCLEIC ACID PROBES FOR THE METHOD, AND METHOD FOR ANALYZING DATA OBTAINED BY THE METHOD

The present application is a Divisional application of U.S. Ser. No. 09/556,127 filed Apr. 20, 2000.

BACKGROUND OF THE INVENTION a) Field of the Invention

This invention relates to a method for determining a concentration of a target nucleic acid, a nucleic acid probe for the process, and a method for analyzing data obtained by the method. Specifically, the present invention is concerned with various methods for determining concentrations of diverse nucleic acids on the basis of a principle that fluorescence emission from of a fluorescent dye decreases when a nucleic acid probe labeled with the fluorescent dye is hybridized to a target nucleic acid, that is., by measuring decreases in fluorescence emissions from fluorescent dyes after hybridization of nucleic acid probes labeled with the fluorescent dyes to target nucleic acids relative to fluorescence emissions from the fluorescent dyes before the hybridization, nucleic acid probes and devices useful for the practice of the methods, methods for analyzing data obtained by PCR which is one of the determination methods, systems provided with means for practicing the analysis methods, and computer-readable recording media with individual procedures of the analysis methods stored therein as programs.

b) Description of the Related Art

A variety of methods are conventionally known to determine a concentration of a nucleic acid by using a nucleic acid probe labeled with a fluorescent dye. These methods include:

(1) Dot blotting assay

After a target nucleic acid and a nucleic acid probe labeled with a fluorescent dye are hybridized on a membrane, unreacted nucleic probe is washed off. The intensity of fluorescence only from fluorescent dye molecules, by which the nucleic acid probe hybridized with the target nucleic acid is labeled, is measured.

(2) Method making use of an intercalator: Glazer et al., Nature, 359, 959, 1992

A certain specific fluorescent dye called "intercalator" emits strong fluorescence upon its insertion into a double strand of a nucleic acid. This method measures an increase in fluorescence from the fluorescent dye. Examples of the fluorescent dye can include ethidium bromide [Jikken Igaku (Laboratory Medicine), 15(7), 46–51, Yodosha (1997)] and SYBR R Green I (LightCycler™ System, Apr. 5, 1999; pamphlet distributed by Roche Diagnostics, Mannheim, Germany).

(3) Method making use of FT (fluorescence energy transfer): Mergny et al., Nucleic Acid Res., 22, 920–928, 1994.

This method comprises hybridizing two nucleic acid-probes to a target nucleic acid. These two nucleic acid probes are labeled by different fluorescent dyes, respectively. The fluorescent dye of one of the two probes can transfer energy to the fluorescent dye of the other probe such that the latter fluorescent dye is caused to emit fluorescence. These two probes are designed such that they hybridize with their fluorescent dyes being located opposite each other and apart from each other by 1 to 9 bases. When these two nucleic acid probes hybridize to the target nucleic acid, emission of fluorescence from the latter fluorescent dye takes place. The intensity of this fluorescence emission is proportional to the number of replications of the target nucleic acid.

(4) Molecular beacon method: Tyagi et al., Nature Biotech., 14, 303–308, 1996

A nucleic acid probe for use in this method is labeled at an end thereof with a reporter dye and at an opposite end thereof with a quencher dye. As both end portions of the probe are complementary with each other in their base sequences, the overall base sequence of the probe is designed to form a hairpin stem. Owing to this structure, emission from the reporter dye is suppressed by the quencher dye under Forster resonant energy in a state suspended in a liquid. When the probe hybridizes to a target nucleic acid, the hairpin stem structure is broken. This leads to an increase in the distance between the reporter pigment and the quencher pigment, so that the transfer of Forster resonant energy no longer takes place. This allows the reporter dye to make emission.

(5) Davis's method: Davis et al., Nucleic Acids Res., 24, 702–706, 1996

This method uses DNA constructs containing one or two fluorescein molecules in flow cytometry. The fluorescein molecules were attached to the 3'end of a DNA probe through an 18-atom spacer arm that resulted in a 10-fold increase in fluorescence intensity compared to the DNA probe to which fluorescein was directly attached to the 3'end of the probe.

Applied to various determination methods for nucleic acids, fluorescent in situ hybridization assays, PCR, ligase chain reactions, strand displacement assays, competitive hybridization and the like, significant developments have been made on these methods.

Although these methods are now widely used, they include a disadvantageous step that, subsequent to hybridization reaction between a nucleic acid probe labeled with a fluorescent dye and a target nucleic acid, an unhybridized portion of the nucleic acid probe has to be washed out of the reaction system. Obviation of this step can apparently bring about shorter determination time, simplified determination, and accurate determination. There is, accordingly, a long-standing desire for the development of a nucleic acid determination method which does not include such a step.

SUMMARY OF THE INVENTION

With the foregoing in view, the present invention has as an object thereof the provision of a method for determining a concentration of a target nucleic acid by using a nucleic acid probe labeled with a fluorescent dye, which makes it possible to determine the concentration of the target nucleic acid in a shorter time, more easily and more accurately.

The present invention also has as other objects the provision of nucleic acid probes and devices useful for the practice of the methods, methods for analyzing data obtained by PCR which is one of the determination methods, systems provided with means for practicing the analysis methods, and computer-readable recording media with individual procedures of the analysis methods stored therein as programs.

To achieve the above-described objects, the present inventors have proceeded with an investigation on methods for determining a concentration of a nucleic acid by using a nucleic acid probe. As a result, it was found that emission of fluorescence from a fluorescent dye decreases (quenching phenomenon of fluorescence) when a nucleic acid probe labeled with the fluorescent dye hybridizes to a target nucleic acid. It was also found that this decrease is significant with certain specific dyes. It was also found that the extent of this decrease varies depending on bases in a probe portion, to which the fluorescent dye is conjugated, or on the sequence of the bases. The present invention has been completed base on these findings.

Therefore, the present invention provides the following methods, probes, kits, systems, recording medium, device and assay:

1) A method for determining a concentration of a target nucleic acid by using a nucleic acid probe labeled with a fluorescent dye, which comprises:
   providing, as the probe, a nucleic acid probe capable of reducing fluorescence emission from the fluorescent dye when hybridized with the target nucleic acid;
   hybridizing the probe to the target nucleic acid; and
   measuring a decrease in fluorescence emission from the fluorescent dye after the hybridization relative to fluorescence emission from the fluorescent dye before the hybridization.

2) A nucleic acid probe for determining a concentration of a target nucleic acid, said probe being labeled with a fluorescent dye, wherein:
   the probe is labeled at an end portion thereof with the fluorescent dye, and
   the probe has a base sequence designed such that, when the probe is hybridized with the target nucleic acid, at least one G (guanine) base exists in a base sequence of the target nucleic acid at a position 1 to 3 bases apart from an end base portion where the probe and the target nucleic acid are hybridized with each other,
   whereby the fluorescent dye is reduced in fluorescence emission when the probe is hybridized with the target nucleic acid; and
   a method for determining a concentration of a target nucleic acid, which comprises hybridizing the above-described nucleic acid probe to the target nucleic acid and measuring a decrease in fluorescence emission from the fluorescent dye after the hybridization relative to fluorescence emission from the fluorescent dye before the hybridization.

3) A method for analyzing or determining polymorphism or mutation of a target nucleic acid or gene, which comprises:
   hybridizing the above-described nucleic acid probe to the target nucleic acid or gene, and
   measuring a change in fluorescence.

4) A kit for analyzing or determining polymorphism or mutation of a target nucleic acid or gene, comprising the above-described nucleic acid probe.

5) A method for analyzing data obtained by the analysis or determination method described above under 3), which comprises the following step:
   correcting a fluorescence intensity of a reaction system, in which the target nucleic acid or gene has been hybridized with the nucleic acid probe labeled with the fluorescent dye, in accordance with a fluorescence intensity of the reaction system before the hybridization.

6) A system for analyzing or determining polymorphism or mutation of a target nucleic acid or gene, comprising means for practicing the data analysis or determination method described above under 5).

7) A computer-readable, recording medium comprising a program recorded therein for making a computer perform the correction step described above under 5).

8) A method for determining a concentration of a target nucleic acid, which comprises using a probe with the nucleic acid probe described above under 1) or 2) bound on a surface of a solid support; and
   a device for determining a concentration of the target nucleic acid, which is useful in practicing the above method.

9) A fluorescent in situ hybridization assay making use of the nucleic acid determination method described above under 1), 2) or 8).

10) A method for analyzing data obtained by the nucleic acid determination method described above under 1), 2) or 9).

11) A PCR method making use of the nucleic acid determination method described above under 1) or 2).

12) A method for analyzing data obtained by the PCR method described above under 11).

13) A method for analyzing a melting curve of a nucleic acid by using the PCR method described above under 11).

14) An analysis method making combined use of the methods described above under 12) and 13), respectively.

15) A PCR determination and/or analysis system provided with means for performing an analysis in accordance with the analysis method described above under 11), 12), 13) or 14).

16) A computer-readable recording medium with procedures, through which an analysis is performed by the analysis method described above under 11), 12), 13) or 14), recorded as a program.

17) A method for quantitating a target nucleic acid, which comprises making use of the data analysis method described above under 12) or 14).

18) A method for determining a concentration of a target nucleic acid, which comprises using the PCR determination and/or analysis system described above under 15).

19) A method for determining a concentration of a target nucleic acid, which comprises using the recording medium described above under 16).

Numerous advantageous effects have been brought about by the present invention as will be set out below.

1) Since use of the nucleic acid determination method, probe or device according to the present invention does not require an operation such as that needed to remove unreacted nucleic acid probe from a determination system, the concentration of a target nucleic acid can be determined in a short time and with ease. When applied to a co-cultivation system of microorganisms or a symbiotic cultivation system of microorganisms, the viable count of a particular microorganism strain in the system can be specifically measured in a short time. Further, the present invention has also provided a simple method for analyzing or determining polymorphism, such as SNP (single nucleotide polymorphism), or mutation of a target nucleic acid or gene.

2) Further, the quantitative PCR method according to the present invention has the following advantageous effects:
   a. As the quantitative PCR method does not involve addition of any factor which may act in an inhibitive manner on amplification of a target nucleic acid by Taq DNA polymerase, quantitative PCR can be conducted under similar conditions as conventionally-known usual PCR having specificity.
   b. The specificity of PCR can be maintained high, so that amplification of primer dimer is retarded. Compared with conventionally-known quantitative PCR, the quantitation limit can be lowered on the order of about one digit.
   c. It is no longer required to provide a complex nucleic acid probe. It is, therefore, possible to save time and cost which would otherwise be required for such a complex nucleic acid probe.

d. A target nucleic acid can be effectively amplified, so that the amplification step can be monitored in real time.

3) Upon analysis of data obtained by the real-time quantitative PCR, the data analysis method according to the present invention can be used to prepare a working line for the determination of the number of copies of a nucleic acid in a nucleic acid sample of unknown nucleic acid copy number. This working line has a correlation coefficient which is far higher than those available by conventional methods. Use of the data analysis method according to the present invention, therefore, makes it possible to accurately determine the number of copies of nucleic acid.

4) A working line the correlation efficient of which is high can be automatically prepared by the use of the data analysis software relating to the analysis method of data obtained by real-time quantitative FCR, the computer-readable recording medium with the procedures of the analysis method recorded as a program therein, or the determination or analysis system for the real-time quantitative PCR. The data analysis software, computer-readable recording medium, and the determination or analysis system all pertain to the present invention.

5) Further, use of the novel method according to the present invention for the analysis of the melting curve of a nucleic acid makes it possible to determine the Tm value of the nucleic acid with high accuracy. Moreover, use of the data analysis software for the method, the computer-readable recording medium with the procedures of the analysis method recorded as a program therein, or the determination or analysis system for the real-time quantitative PCR makes it possible to obtain an accurate Tm value.

BRIEF DESCRIPTION OF THE DRAWINGS

FIG. 2 diagrammatically illustrates effects of heat treatment of 16S rRNA on hybridization of a 35-nucleotides-chained 2-O—Me probe to a target nucleic acid, in which:

Dashed curve: Heated 16S rRNA was added to a solution of the probe, and

Figure 3:
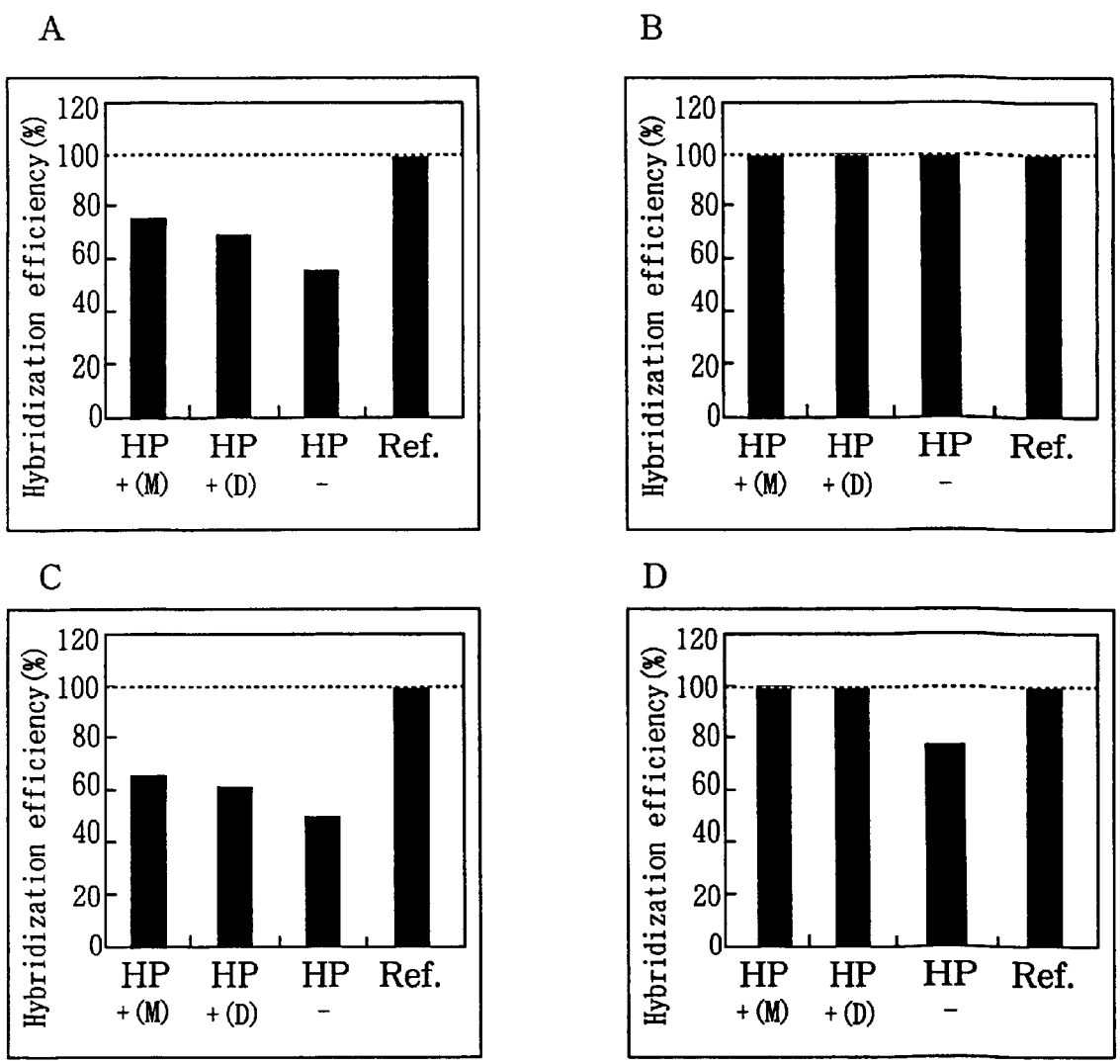
Figure 4:
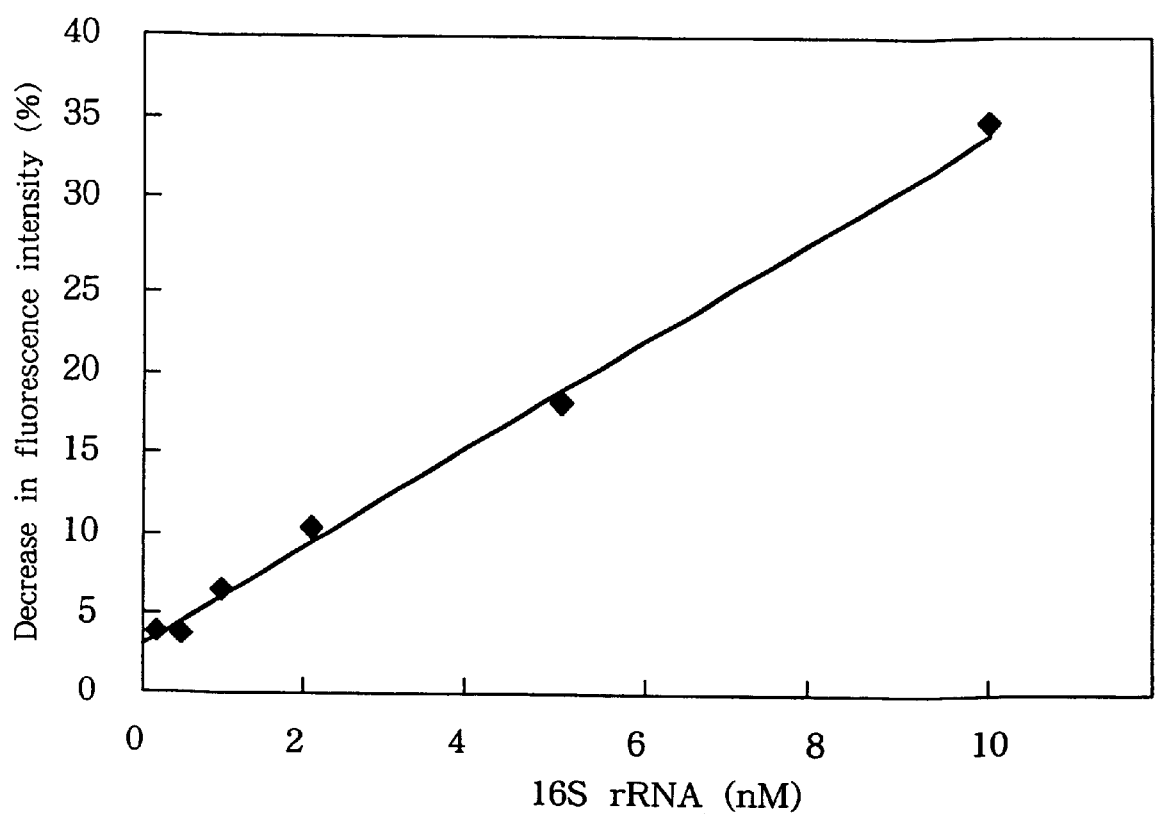
Figure 5:
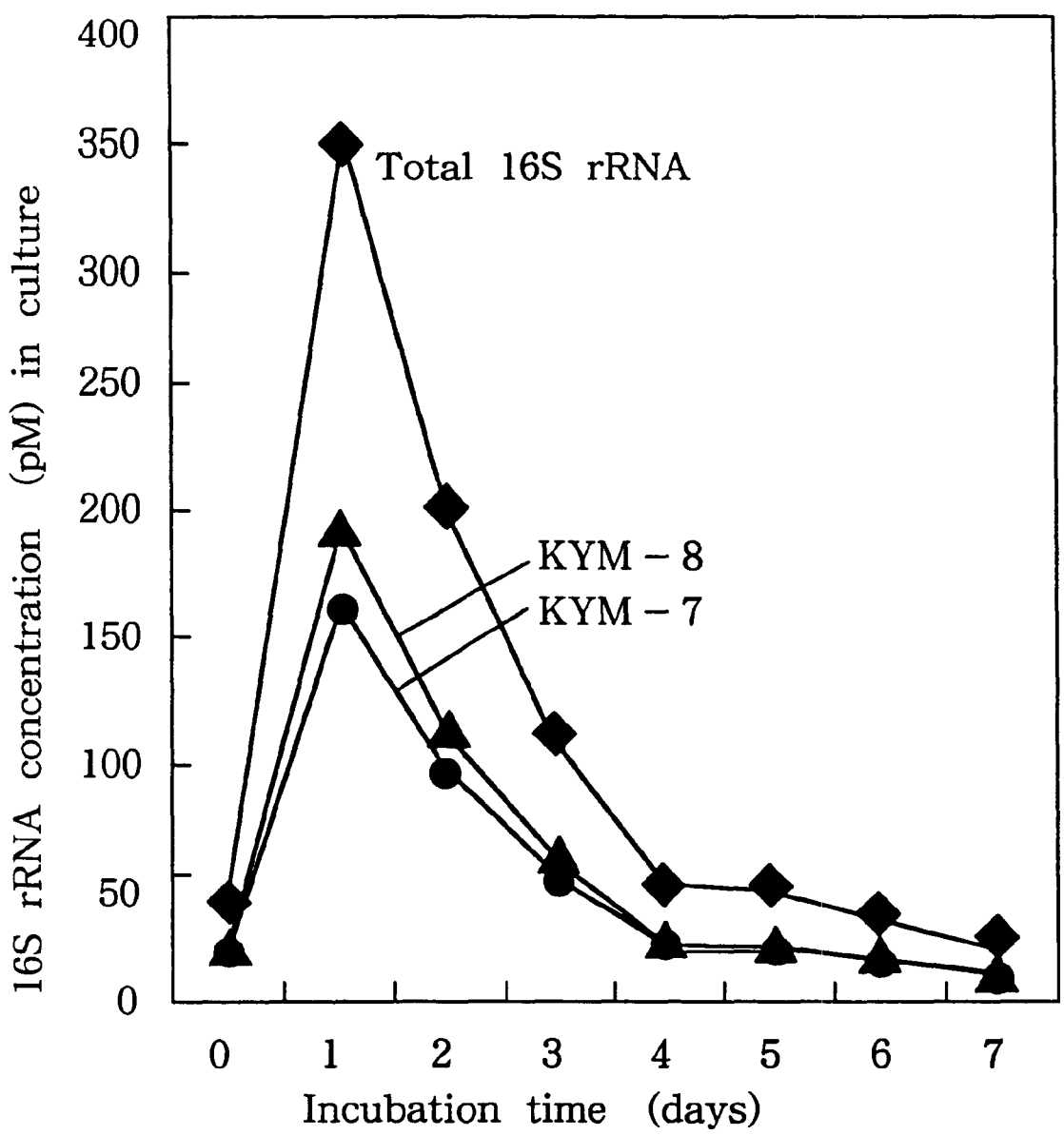
Figure 6:
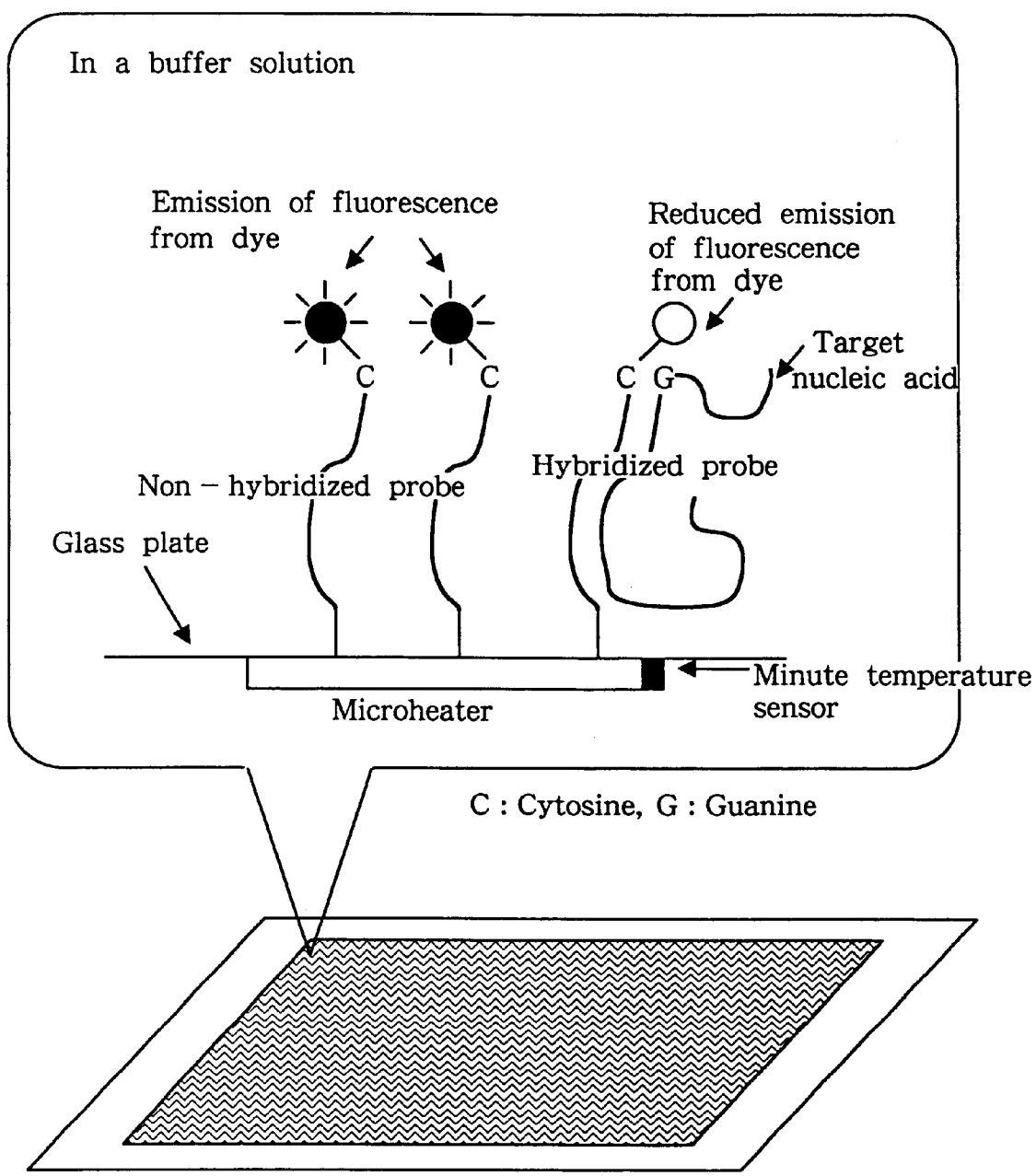
Figure 7:
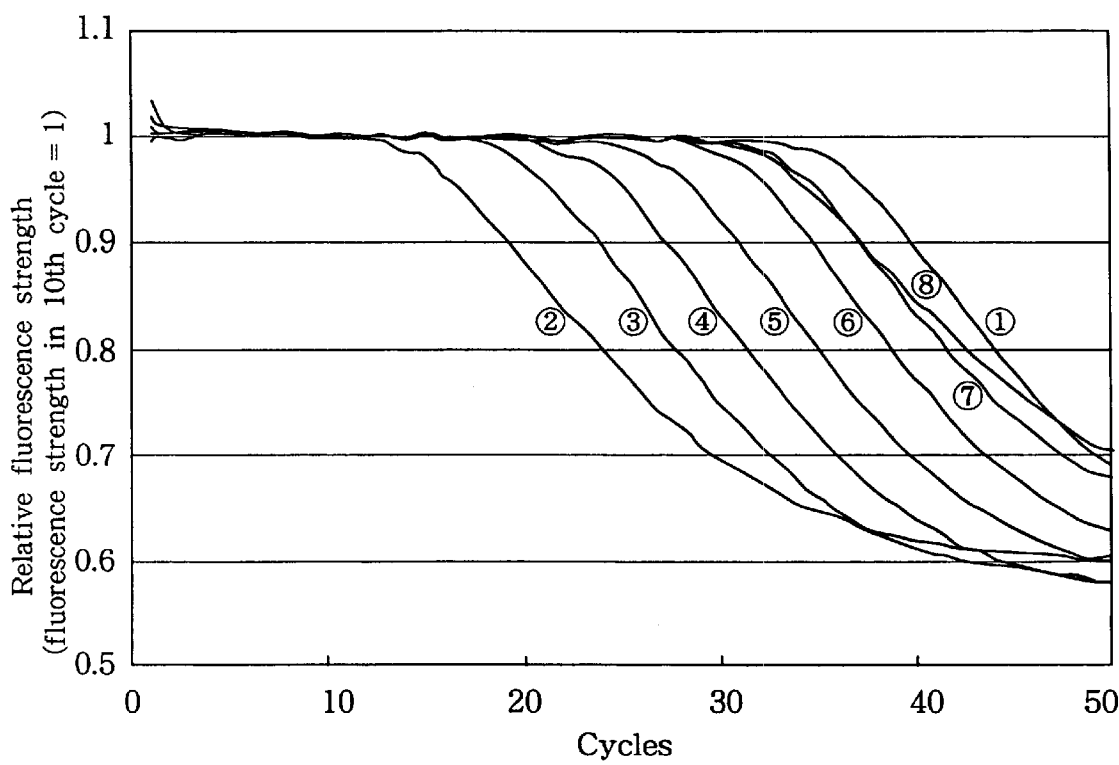

Solid curve: Non-heated 16S rRNA was added to a solution of the probe;

FIG. 3 diagrammatically shows effects of methylation of 2'-OH of ribose in the 5' terminal residue of the probe, the number of nucleotide-chain of the probe and the helper probes on the hybridization of the probes to the target 16S rRNA;

FIG. 4 shows a working curve of rRNA assay by an invention method;

FIG. 5 diagrammatically shows analysis results of time-dependent rRNA of the strains, KYM-7 and CYM-8, in co-cultivation by an in situ hybridization assay method with the invention technique;

FIG. 6 is a schematic illustration of a DNA chip according to the present inventions;

FIG. 7 diagrammatically illustrates a relationship between cycles and a decrease in fluorescence emission from a fluorescent dye in a real-time quantitative PCR method making use of primers 1 and 2 labeled with BODIPY FL, in which signs ① to ⑧ have the following meanings:

① Number of copies of *E. coli* genome DNA: 0; primer: primer 1+primer 2.

② Number of copies of *E. coli* genome DNA: $2.4 \times 10^6$; primer: primer 1+primer 2.

③ Number of copies of *E. coli* genome DNA: $2.4 \times 10^5$; primer: primer 1+primer 2.

④ Number of copies of *E. coli* genome DNA: $2.4 \times 10^4$; primer: primer 1+primer 2.

⑤ Number of copies of *E. coli* genome DNA: $2.4 \times 10^3$; primer: primer 1.

⑥ Number of copies of *E. coli* genome DNA: $2.4 \times 10^2$; primer: primer 1.

⑦ Number of copies of *E. coli* genome DNA: $2.4 \times 10^1$; primer: primer 1.

⑧ Number of copies of *E. coli* genome DNA: $2.4 \times 10^0$; primer: primer 1.

Figure 8:
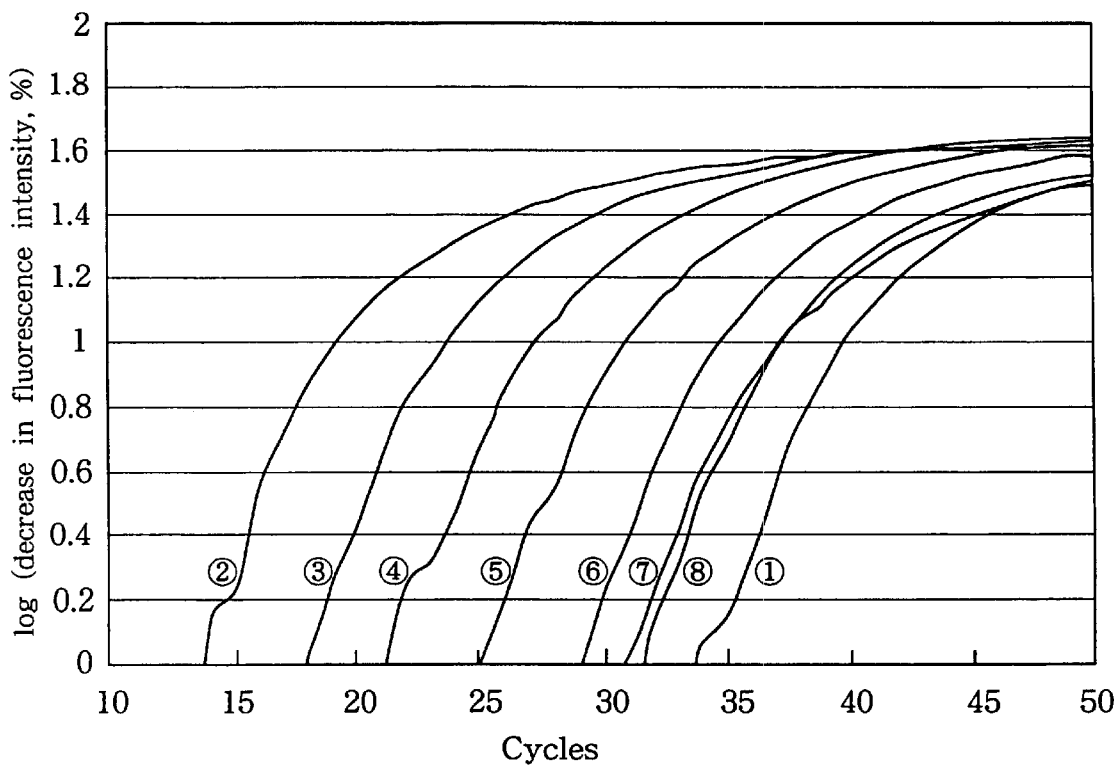
Figure 9:
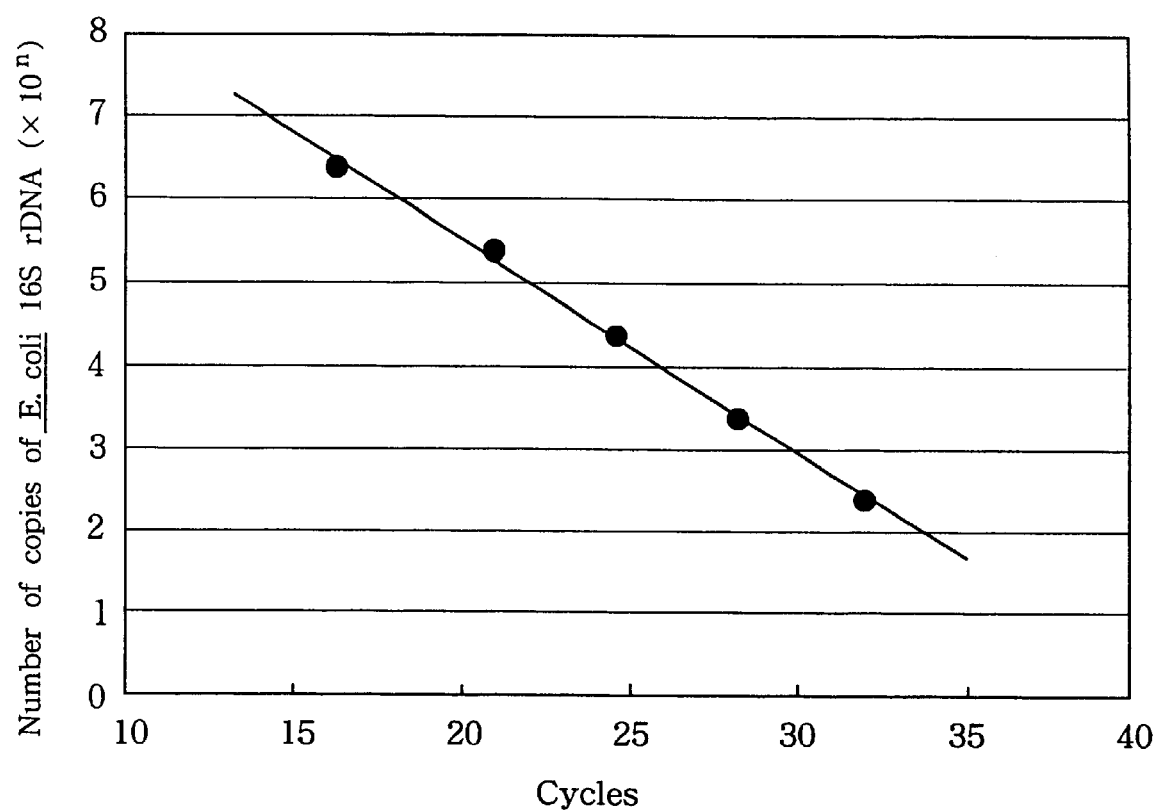
Figure 10:
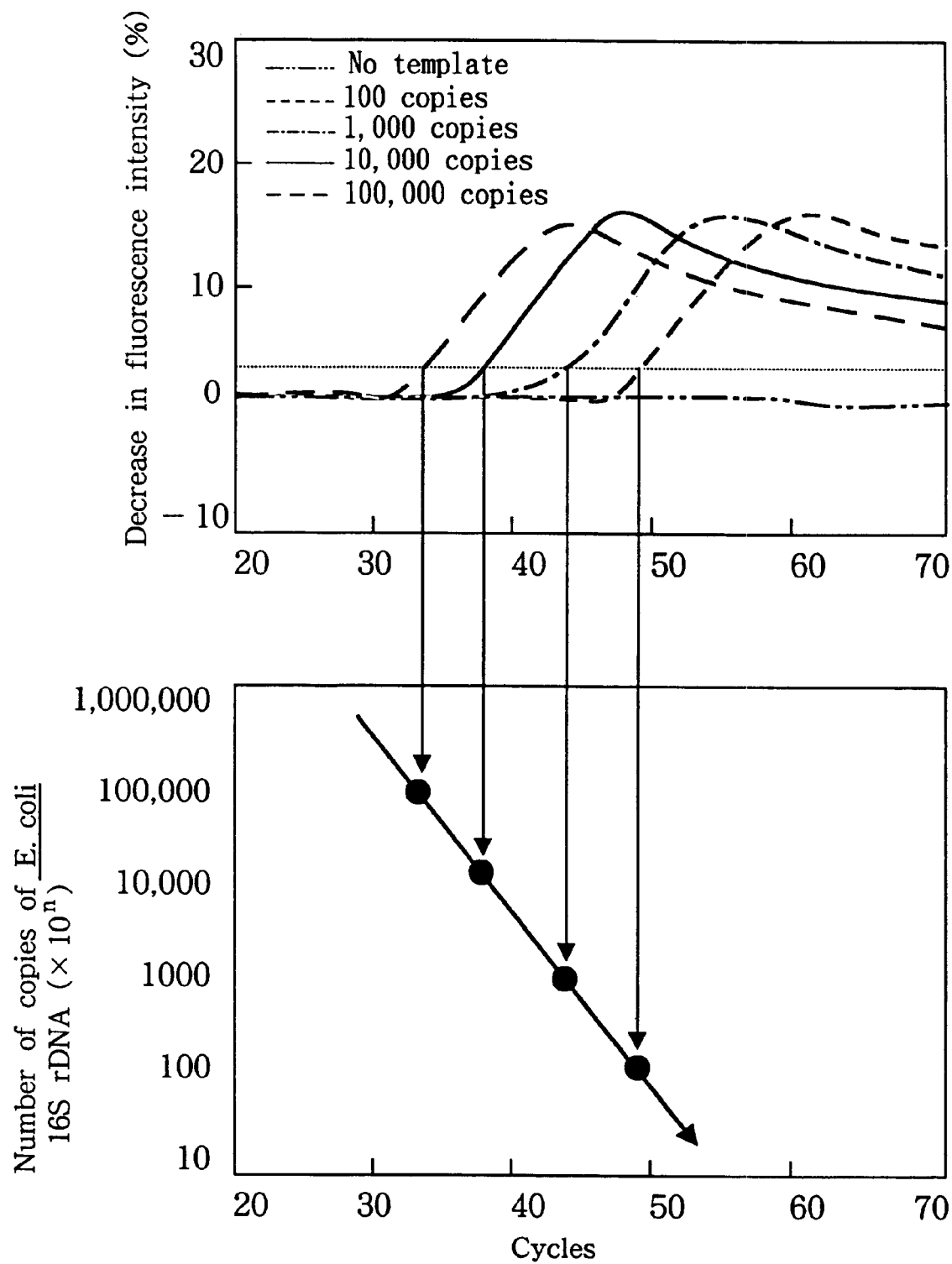
Figure 11:
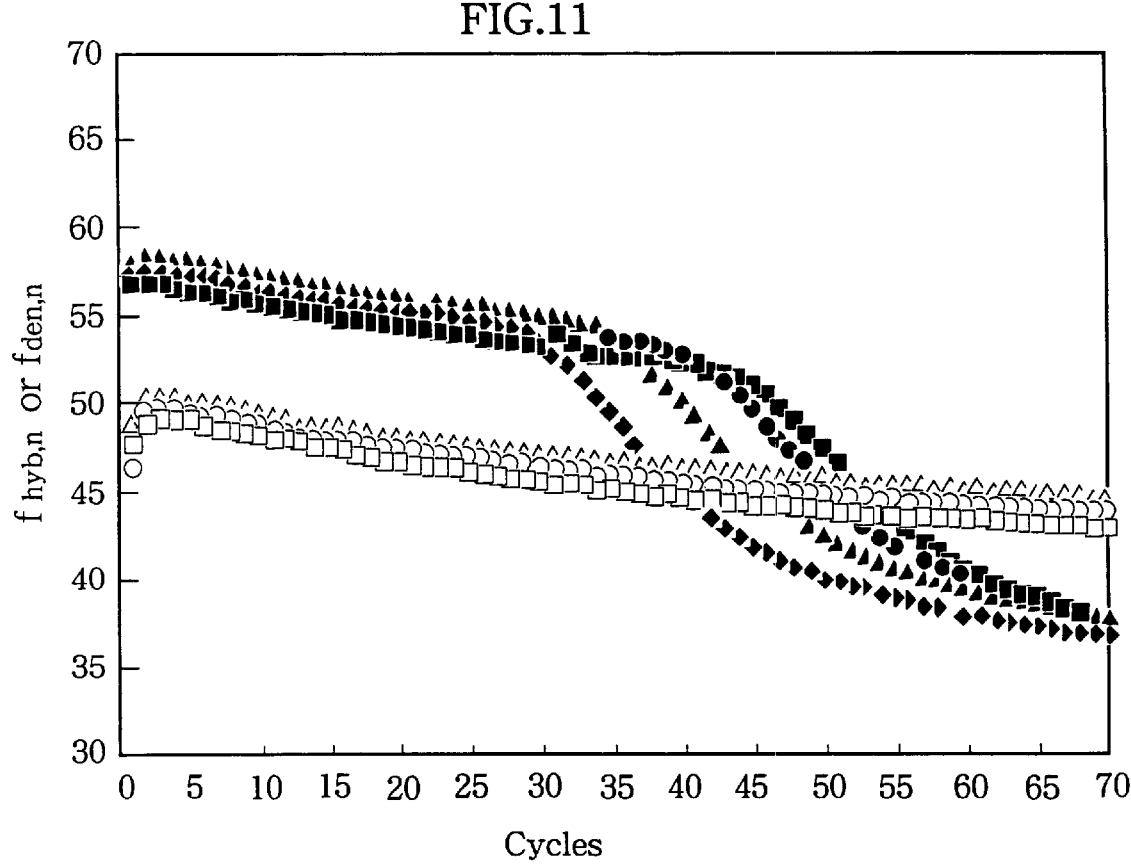

FIG. 8 diagrammatically shows a relationship between cycles and the logarithm of a decrease in fluorescence emission from a fluorescent dye in the real-time quantitative PCR making use of primers 1 and 2 labeled with BODIPY FL, in which signs ① to ⑧ have the same meanings as defined above in connection with FIG. 7;

FIG. 9 is a diagram showing a working line for 16S rDNA of *Escherichia coli,* which was prepared using the real-time quantitative PCR according to the present invention;

FIG. 10 (upper diagram) depicts decreases (%) in fluorescence intensity in real-time quantitative PCR according to the present invention in which a single probe of the present invention was used as opposed to two probes required for a conventional real-time quantitative PCR method using FRET;

FIG. 10 (lower diagram) shows a working line for 16S rDNA of *Escherichia coli,* and the working line depicts a relationship between the number of copies of the 16S rDNA and starting cycles (threshold cycle numbers) in each copy of the nucleic acid at which the decrease in fluorescence emission was capable of being significantly observed in the upper diagram;

FIG. 11 depicts fluorescence decrease curves obtained by real-time quantitative PCR according to the present invention, which used a primer labeled with BODIPY FL, without performing correction processing according to the present invention, in which:

■ Target nucleic acid: 10 copies: Temperature of the reaction system upon measurement of fluorescence intensity: 72° C.

● Target nucleic acid: 100 copies; Temperature of the reaction system upon measurement of fluorescence intensity: 72° C.

▲ Target nucleic acid: 1,000 copies; Temperature of the reaction system upon measurement of fluorescence intensity: 72° C.

◆ Target nucleic acid: 10,000 copies; Temperature of the reaction system upon measurement of fluorescence intensity: 72° C.

□ Target nucleic acid: 10 copies; Temperature of the reaction system upon measurement of fluorescence intensity: 95° C.

○ Target nucleic acid: 100 copies; Temperature of the reaction system upon measurement of fluorescence intensity: 95° C.

△ Target nucleic acid: 1,000 copies; Temperature of the reaction system upon measurement of fluorescence intensity: 95° C.

◇ Target nucleic acid: 10,000 copies; Temperature of the reaction system upon measurement of fluorescence intensity: 95° C.

Figure 12:
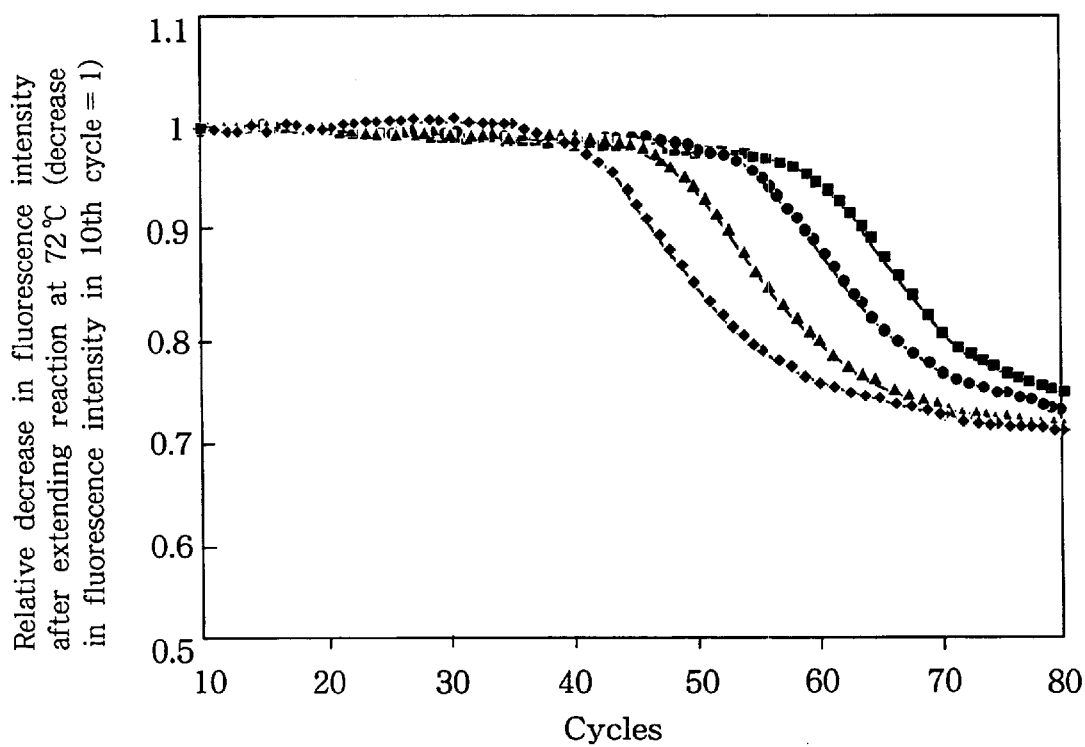

FIG. 12 shows fluorescence decrease curves obtained by the real-time quantitative PCR according to the present invention as in FIG. 11 except that on each of the curves, each decrease (%) in fluorescence emission was corrected assuming that the corresponding value in the $10^{th}$ cycle was 1, in which:
- ■ Target nucleic acid: 10 copies; Temperature upon measurement of fluorescence intensity: 72° C.
- ● Target nucleic acid: 100 copies; Temperature upon measurement of fluorescence intensity: 72° C.
- ▲ Target nucleic acid: 1,000 copies; Temperature upon measurement of fluorescence intensity: 72° C.
- ◆ Target nucleic acid: 10,000 copies; Temperature upon measurement of fluorescence intensity: 72° C.

Figure 13:
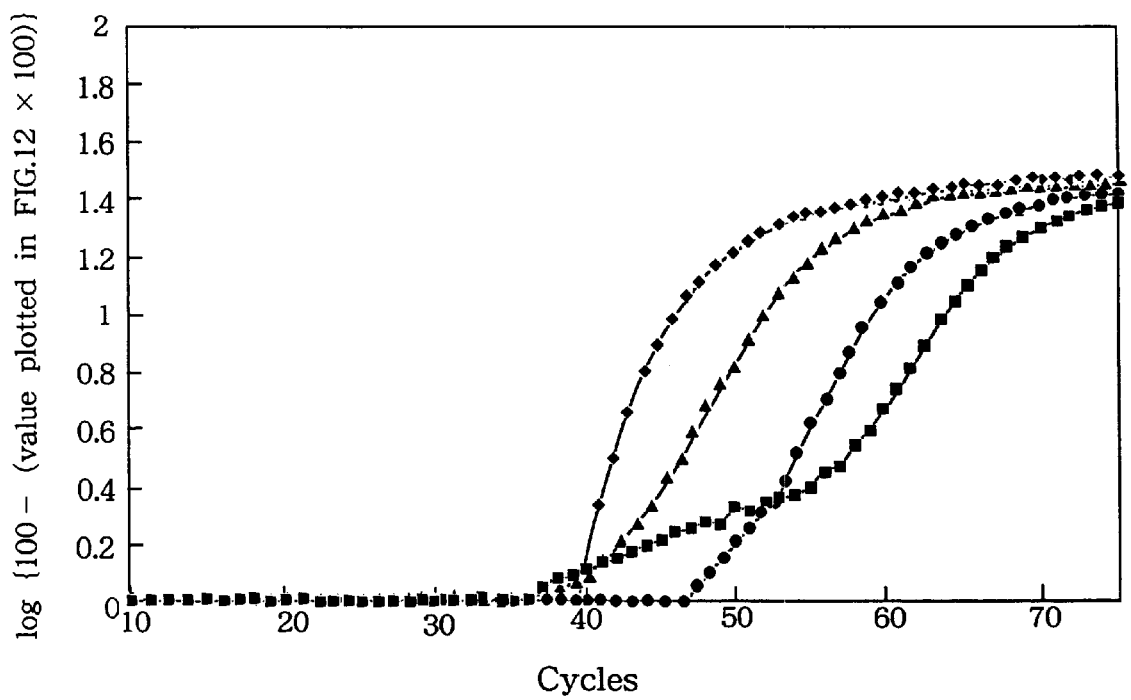

FIG. 13 shows curves obtained by calculating, with respect to the individual plotted values on the respective curves in FIG. 12, the rates of decreases (the rates of changes) in fluorescence intensity in accordance with the formula (9) and then plotting the thus-calculated, in which:
- ■ Target nucleic acid: 10 copies.
- ● Target nucleic acid: 100 copies.
- ▲ Target nucleic acid: 1,000 copies.
- ◆ Target nucleic acid: 10,000 copies.

Figure 14:
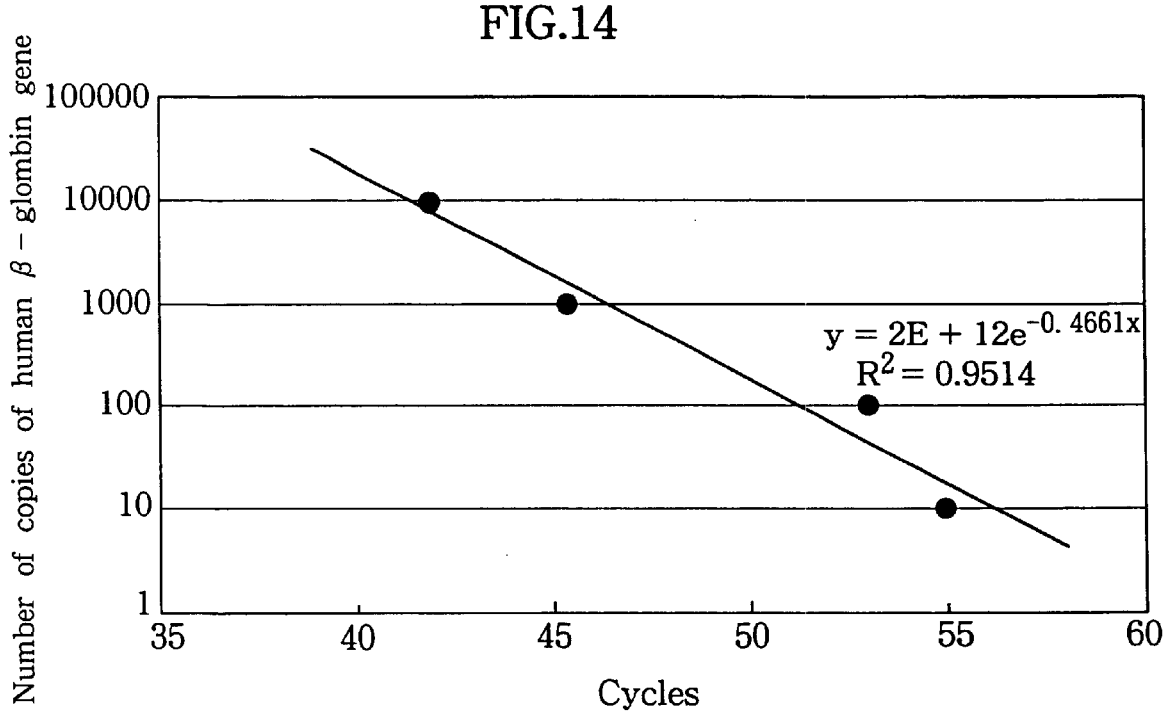

FIG. 14 shows a working line for human genome DNAs as obtained from the data in FIG. 13, in which:
- y: Number of copies of human β-globin gene,
- x: cycles (Ct), and
- $R^2$: correlation coefficient.

Figure 15:
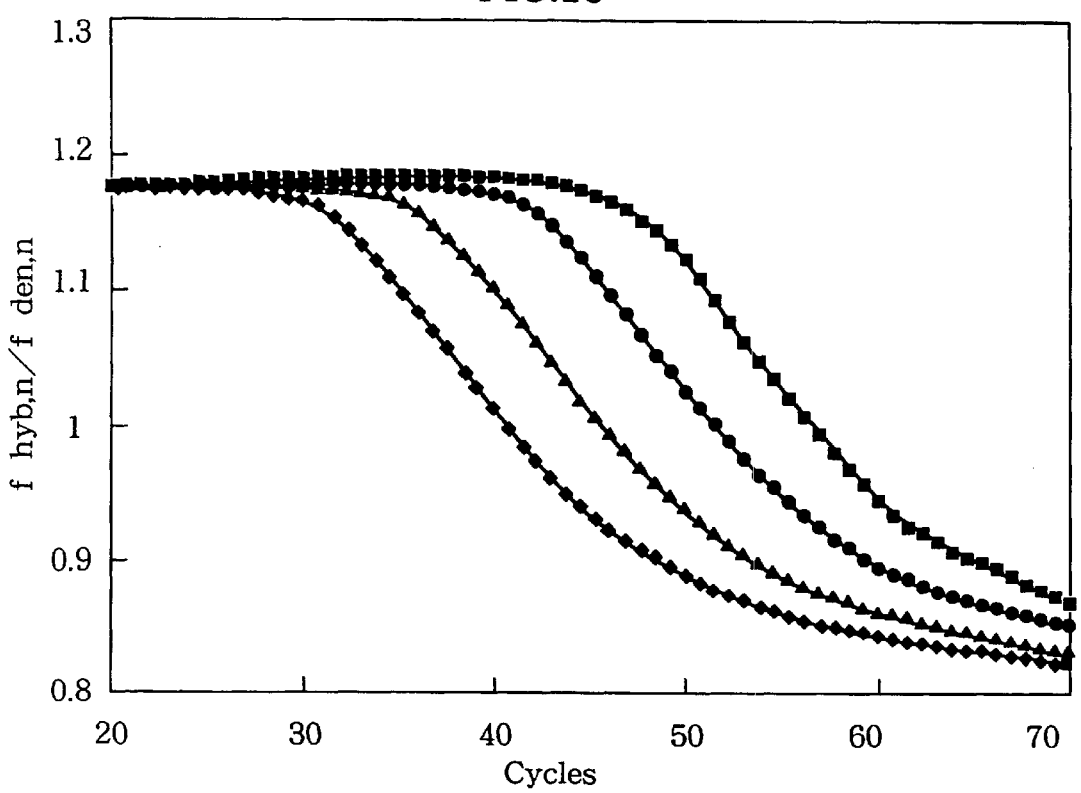

FIG. 15 depicts curves obtained by subjecting the measurement values in the individual cycles in FIG. 11 to correction processing in accordance with the formula (1) and then plotting the corrected values relative to their corresponding cycles, in which:
- ■ Target nucleic acid: 10 copies.
- ● Target nucleic acid: 100 copies.
- ▲ Target nucleic acid: 1,000 copies.
- ◆ Target nucleic acid: 10,000 copies.

Figure 16:
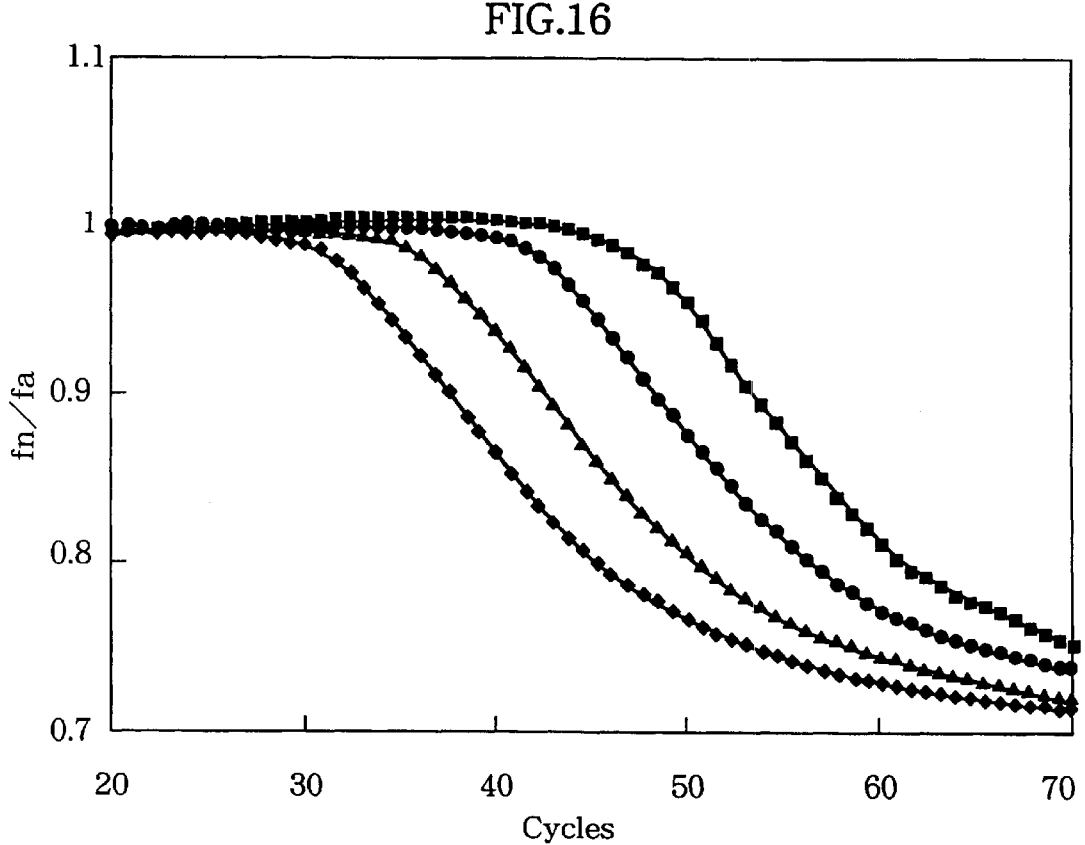

FIG. 16 illustrates curves obtained by plotting values, which have been obtained by processing the processed values of the individual cycles in FIG. 15 in accordance with the formula (3), against their corresponding cycles, in which
- ■ Target nucleic acid: 10 copies.
- ● Target nucleic acid: 100 copies.
- ▲ Target nucleic acid: 1,000 copies.
- ◆ Target nucleic acid: 10,000 copies.

Figure 17:
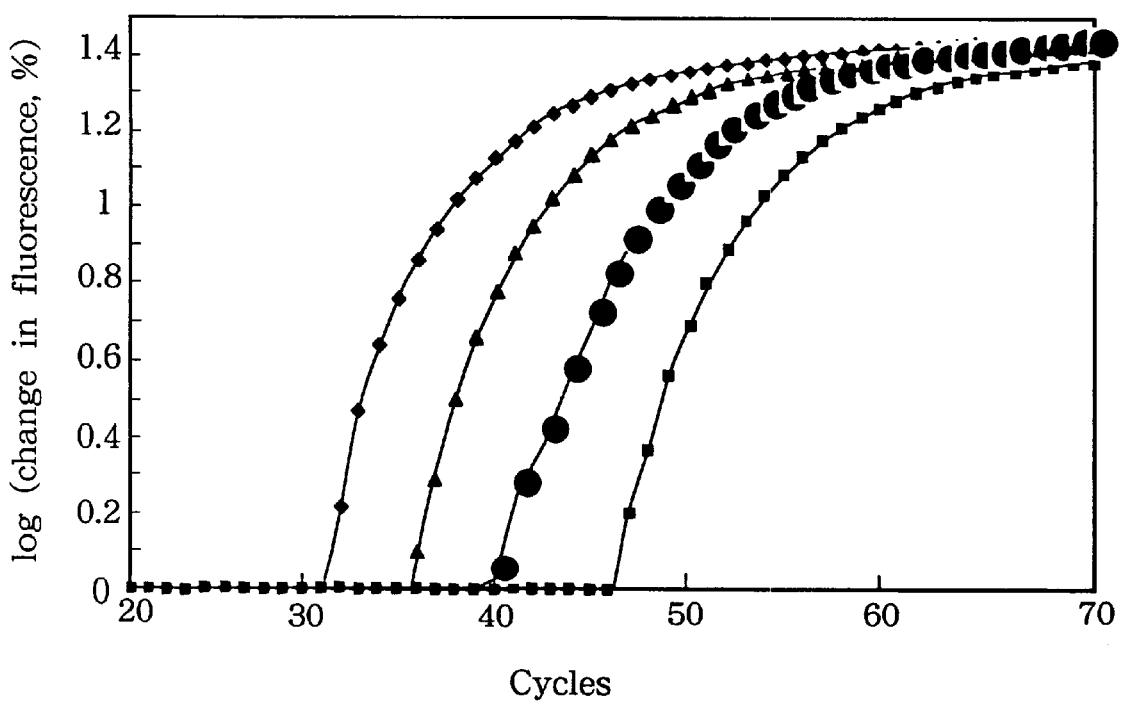

FIG. 17 shows curves obtained by subjecting the corrected values in the individual cycles in FIG. 16 to correction processing in accordance with the formula (6) and then plotting the corrected values relative to their corresponding cycles, in which:
- ■ Target nucleic acid: 10 copies.
- ● Target nucleic acid: 100 copies.
- ▲ Target nucleic acid: 1,000 copies.
- ◆ Target nucleic acid: 10,000 copies.

Figure 18:
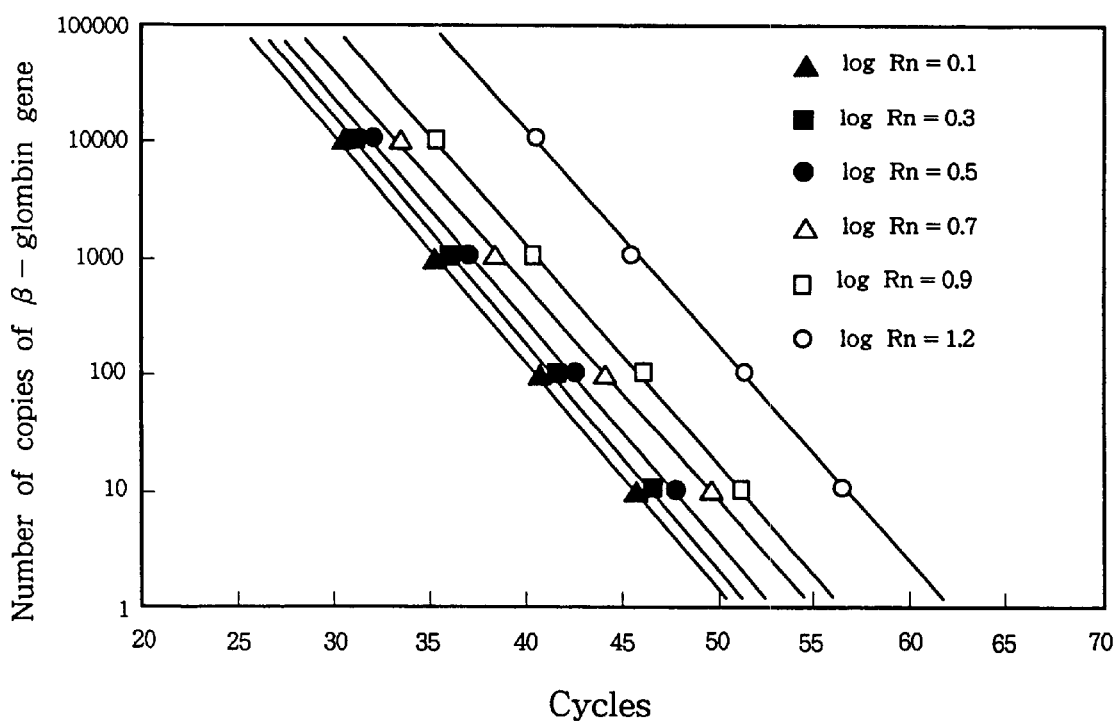

FIG. 18 shows working lines drawn corresponding to 0.1, 0.3, 0.5, 0.7, 0.9 and 1.2 chosen at will as candidates for threshold cycle numbers from the respective values of log (changes in fluorescence, %) in FIG. 16, in which the individual working lines have the following correlation coefficients:
- ▲ log (change in fluorescence, %)=0.1; correlation coefficient: 0.998
- ■ log (change in fluorescence, %)=0.3; correlation coefficient: 0.999
- ● log (change in fluorescence, %)=0.5; correlation coefficient: 0.9993
- Δ log (change in fluorescence, %)=0.7 correlation coefficient: 0.9985
- □ log (change in fluorescence, %)=0.9 correlation coefficient: 0.9989
- ○ log (change in fluorescence, %)=1.2 correlation coefficient: 0.9988

Figure 19:
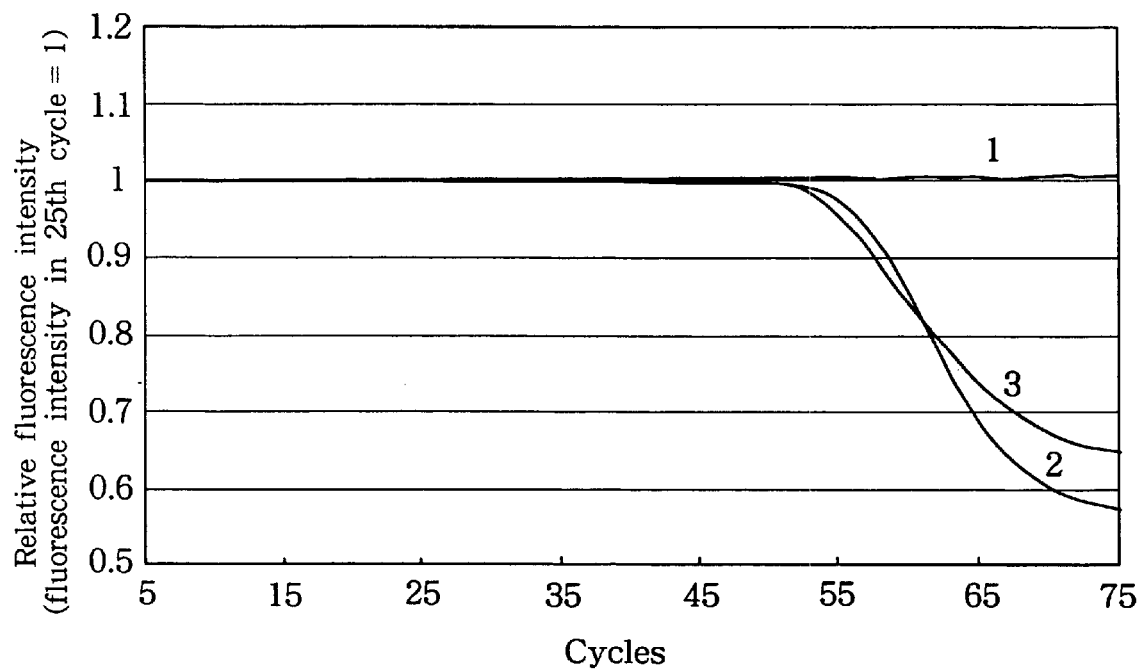
Figure 20:
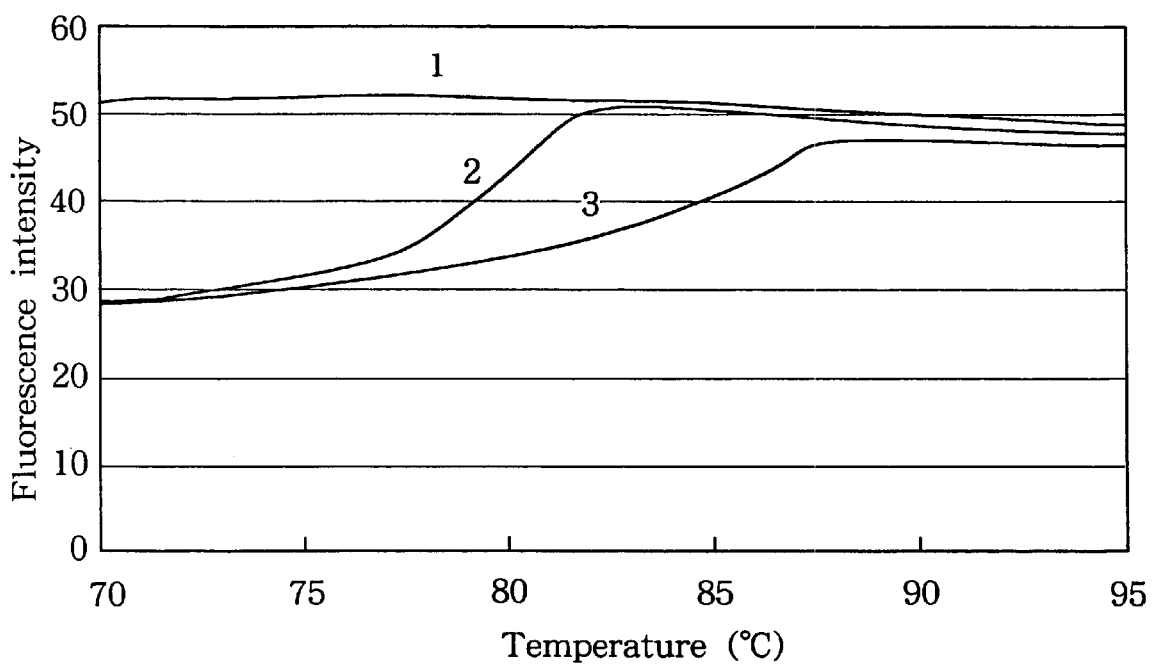
Figure 21:
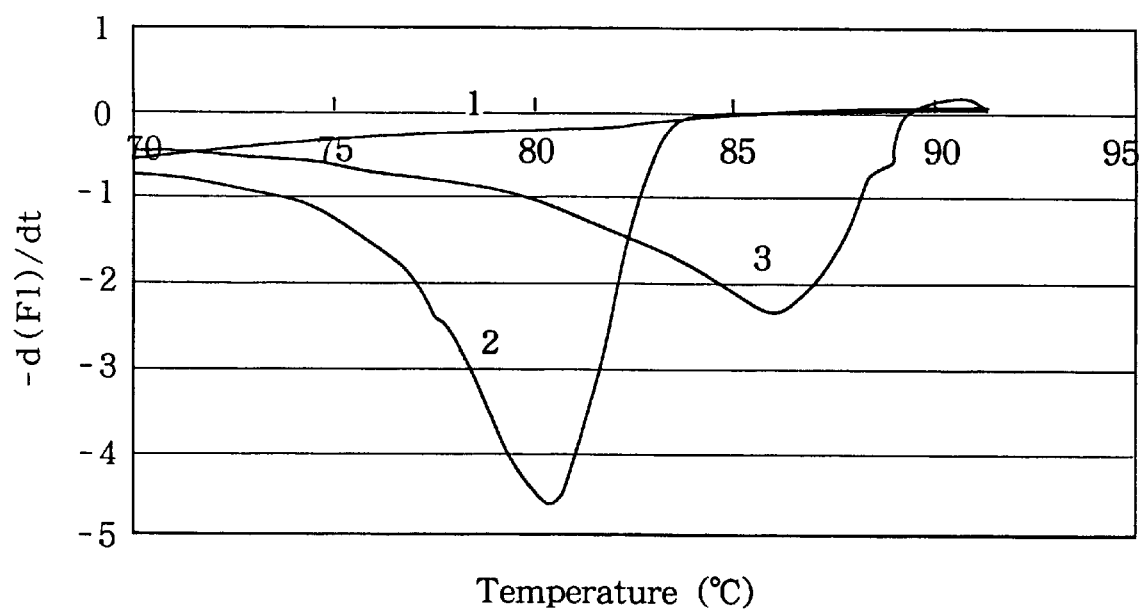

FIG. 19 depicts fluorescence decrease curves when real-time quantitative PCR according to the present invention was conducted on human genome DNA of 1 copy and 10 copies by using the primer labeled with BODIPY FL and the correction processing of the formula (1) was applied, in which:
1: target nucleic acid=0 copy,
2: target nucleic acid=1 copy, and
3: target nucleic acid=10 copies;

FIG. 20 illustrates melting curves of nucleic acids when a melting curve analysis was conducted with respect to the PCR amplification products shown in FIG. 19, in which;
1: target nucleic acid=0 copy,
2: target nucleic acid=1 copy, and
3: target nucleic acid 10 copies; and FIG. 21 illustrates curves obtained by differentiating the curves of FIG. 20 and showing Tm values as valleys, in which:
2: target nucleic acid: 1 copy, and
3: target nucleic acid: 10 copies.

DETAILED DESCRIPTION OF THE INVENTION AND PREFERRED EMBODIMENTS

The present invention will next be described in further detail based on certain preferred embodiments.

The terms as used herein—such as DNAs, RNAs, cDNAs, mRNAs, rRNAs, XTPs, dXTPs, NTPs, dNTPs, nucleic acid probes, helper nucleic acid probes (or nucleic acid helper probes, or simply helper probes), to hybridize, hybridization, intercalators, primers, annealing, extending reactions, thermal denaturing reactions, nucleicacidmeltingcurves, PCR, RT-PCR, RNA-primed PCR, stretch PCR, reverse RCR, PCR using mixed primers, PCR using PNA, hybridization assays, fluorescent in situ hybridization assays, polymerase chain assays (PCR methods), ligase chain reactions, strand displacement assays, competitive hybridization, DNA chips, nucleic acid detecting (gene-getecting) devices, SNP (single nucleotide polymorphism), and co-cultivation systems of plural microorganisms—have the same meanings as the corresponding terms generally employed these days in molecular biology, genetic engineering, bioengineering and the like.

A first feature of the present invention resides in that, in a method for determining a concentration of a target nucleic acid by using a nucleic acid probe labeled with a fluorescent dye, a decrease in fluorescent emission from the fluorescent dye, said decrease taking place upon hybridization of the nucleic acid probe to the target nucleic acid, in other words, a decrease in fluorescent emission from the fluorescent dye after the hybridization relative to fluorescent emission from the fluorescent dye before the hybridization is measured.

The expression "measurement of a target nucleic acid" as used herein means quantitation or quantitative detection of the target nucleic acid or mere detection of the target nucleic acid.

The expression "method for determining a concentration of a target nucleic acid by using a nucleic acid probe labeled with a fluorescent dye" means a hybridization assay, fluorescent in situ hybridization assay, polymerase chain assay (PCR method), ligase chain reaction, strand displacement assay, competitive hybridization or the like. According to these methods, subsequent to addition of a nucleic acid probe labeled with a fluorescent dye, the fluorescent dye in the unreacted nucleic acid probe not hybridized with a target nucleic acid is removed from the determination system by washing or the like. The fluorescent dye, with which the nucleic acid probe hybridized with the target nucleic acid is labeled, is caused to emit fluorescence from the probe directly or by applying an indirect measure to the probe (for example, causing an enzyme to act), and the intensity of the fluorescence is measured. The present invention is characterized in that a concentration of a target nucleic acid is determined without needing such a complex operation.

The term "target nucleic acid" as used herein means a nucleic acid the quantitation or qualitative detection or mere detection of which is intended, irrespective whether it is in a purified form or not and further irrespective of its concentration. Various other nucleic acids may also exist together with the target nucleic acid. For example, the target nucleic acid may be a specific nucleic acid in a co-cultivation system microorganisms (a mixed system of RNAs or gene DNAs of plural microorganisms) or a symbiotic cultivation system of microorganisms (a mixed system of RNAs or gene DNAs of plural animals, plants and/or microorganisms), the quantitation or qualitative detection or mere detection of which is intended. Purification of the specific nucleic acid, if needed, can be conducted by a method known per se in the art. For example, purification can be effected using a purification kit or the like available on the market. Specific examples of the above-described nucleic acid can include DNAs, RNAs, PNAs, 2-O—MeRMAs, deoxyribooligonucleotides, and riboxyorigonucleotides.

In the present invention, fluorescent dyes commonly employed for the determination or detection of nucleic acids by labeling nucleic acid probes may be conveniently used. It is, however, preferred to use fluorescent dyes the fluorescence emission from each of which decreases when a nucleic acid probe labeled with the fluorescent dye is hybridized to a target nucleic acid. Illustrative of such fluorescent dyes are fluorescein and derivatives thereof [for example, fluorescein isothiocyanate (FITC) and its derivatives]; Alexa 488, Alexa 532, cy3, cy5, EDANS (5-(2'-aminoethyl)amino-1-naphthalene sulfonic acid); rhodamine 6G (R6G) and its derivatives [for example, tetramethylrhodamine (TMR), tetramethylrhodamine isothiocyanate (TMRITC), x-rhodamine, Texas red, "BODIPY FL" (trade name, product of Molecular Probes, Inc. (Eugene, Oreg., U.S.A.), "BODIPY FL/C3" (trade name, product of Molecular Probes, Inc.), "BODIPY FL/C6" (trade name, product of Molecular Probes, Inc.), "BODIPY 5-FAM" (trade name, product of Molecular Probes, Inc.), "BODIPY TMR" (trade name, product of Molecular Probes, Inc.), and derivatives thereof (for example, "BODIPY TR" (trade name, product of Molecular Probes, Inc.), "BODIPY R6G" (trade name, product of Molecular Probes, Inc.), "BODIPY 564" (trade name, product of Molecular Probes, Inc.), and "BODIPY 581" (trade name, product of Molecular Probes, Inc.)]. Among these, FITC, EDANS, TMR, Alexa 488, Alexa 532, "BODIPY FL/C3" and "BODIPY FL/C6" are preferred, with Alexa 488, Alexa 532, "BODIPY FL/C3" and "BODIPY FL/C6" being more preferred.

The nucleic acid probe which is to be hybridized to the target nucleic acid may be formed of either an oligodeoxyribonucleotide or an oligoribonucleotide. The nucleic acid probe may be a chemiric oligonucleotide which contains both of them. It is also possible to use a 2'-o-methyloligoribonucleotide in which the nucleoside portion at the 5'end of the oligoribonucletide is cytidine and the 2'-OH group of the cytidine is modified by a methyl group. To enhance affinity with RNA, the 2'-o-methyloligoribonucleotide may be inserted in an oligodeoxynucleotide.

Incidentally, a nucleic acid probe with modified DNA, such as 2'-o-methyloligoribonucleotide, inserted in an oligodeoxynucleotide is used primarily for the determination of RNA. Upon determination of RNA by the probe, it is preferred to subject an RNA solution as a sample to heat treatment at 80 to 100° C., preferably 90 to 100° C., most preferably 93 to 97° C. for 1 to 15 minutes, preferably 2 to 10 minutes, most preferably 3 to 7 minutes before hybridization with the probe such that the higher-order structure of RNA can be degraded. Where the base strand of the nucleic acid probe is formed of 35 or fewer bases, addition of a helper probe, for example, an oligonucleotide the base sequence of which is (5')AGGCCGGCCCTTGACTTTCCT (3') to a reaction mixture is preferred for raising the efficiency of the hybridization to the sequence region. In this case, the helper probe can be in an oligodeoxyribonucleotide form or in a 2'-o-methyloligo-ribonucleotide form. When a nucleic acid probe longer than a 35-base strand is used, however, it is only necessary to thermally denature target RNA. When the nucleic acid probe according to the present invention is hybridized to RNA as described above, the fluorescence intensity decreases corresponding to the concentration of RNA in the reaction mixture, and RNA can be determined to a final RNA concentration of about 150 pM.

In determination of RNA by a conventional hybridization assay making use of a nucleic acid probe, an oligodeoxyribonucleotide or oligoribonucleotide has been used as the nucleic acid probe. Because RNA itself has a higher-order solid structure, the efficiency of hybridization between the probe and the target RNA was poor, resulting in quantitation of low accuracy. The conventional methods, therefore, are accompanied by irksomeness that a hybridization reaction is conducted after denaturing RNA and immobilizing denatured RNA on a membrane. The method according to the present invention, on the other hand, uses a nucleic acid probe a ribose portion of which has been modified to have high affinity to a particular structural part of RNA, so that a hybridization reaction can be conducted at a higher temperature compared with the conventional methods. The above-mentioned adverse effects of the high-order structure of RNA can be overcome by simply conducting thermal denaturation as pretreatment and using a helper probe in combination. As a consequence, the efficiency of hybridization in the method according to the present invention is practically as high as 100%, leading to improvements in the accuracy of quantitation. Further, the method according to the present invention is far simpler and easier than the conventional methods.

The probe according to the present invention is formed of 5 to 50 bases, preferably 10 to 25 bases, most preferably 15 to 20 bases. A base number greater than 50 leads to lower permeability through a cell membrane when employed in a fluorescent in situ hybridization assay, thereby narrowing an applicable range of the present invention. A base number smaller than 5, on the other hand, tends to induce non-specific hybridization and, therefore, results in a large determination error.

No particular limitation is imposed on the base sequence of the probe insofar as the probe hybridizes specifically to the target nucleic acid. Preferably, however, the base sequence of the probe may be designed such that, when the nucleic acid probe labeled with the fluorescent dye is hybridized with the target nucleic acid, (1) at least one G (guanine) base exists in the base sequence of the target nucleic acid at a position 1 to 3 bases apart from an end base portion where the probe and the target nucleic acid are hybridized with each other, or (2) base pairs in a probe-nucleic acid hybrid complex form at least one G (guanine) and C (cytosine) pair at the end portion.

The oligonucleotide in the nucleic acid probe in the present invention can be produced by a conventional production process for general oligonucleotides, It can be produced, for example, by a chemical synthesis process or by a microbial process which makes use of a plasmid vector, a phage vector or the like (Tetrahedron Letters, 22, 1859–1862, 1981; Nucleic Acids Research, 14, 6227–6245, 1986). Further, it is suitable to use a nucleic acid synthesizer currently available on the market (for example, "ABI394", trade name, manufactured by Perkin-Elmer Corp., Norwalk, Conn. U.S.A.).

To label the oligonucleotide with the fluorescent dye, desired one of conventionally-known labeling methods can be used (Nature Biotechnology, 14, 303–308, 1996; Applied and Environmental Microbiology, 63, 1143–1147, 1997; Nucleic Acids Research, 24, 4532–4535, 1996). To conjugate a fluorescent dye molecule to the 5'end, a spacer, for example, —$(CH_2)_n$—SH is first introduced into a phosphate group at the 5'end by a method known per se in the art. As such a spacer-introduced derivative is available on the market, a commercial product may be purchased (Midland Certified Reagent Company), In the above-mentioned example, n ranges from 3 to 8 with 6 being preferred. A labeled oligonucletide can be synthesized by conjugating an SH-reactive fluorescent pigment or a derivative thereof with the spacer. The thus-synthesized oligonucleotide, which is labeled with the flurorescent dye, can be purified by reversed phase chromatography or the like to provide a nucleic acid probe for use in the present invention.

Further, the fluorescent dye can be conjugated to the 3'end of the oligonucleotide. In this case, a spacer, for example, —$(CH_2)_n$—$NH_2$ is introduced onto an OH group on the C atom at the 3'-position of ribose or deoxyribose. As such a spacer-introduced derivative is also available on the market like the above-described ones, a commercial product may be purchased (Midland Certified Reagent Company). As an alternative, a phosphate group may be introduced, followed by the introduction of a spacer, for example, —$(CH_2)_n$—SH onto the OH group of the phosphate group. In these cases, n ranges from 3 to 8, with 4 to 7 being preferred. A labeled oligonucletide can be synthesized by conjugating an amino- or SH-reactive fluorescent pigment or a derivative thereof with the spacer. The thus-synthesized oligonucleotide, which is labeled with the flurorescent dye, can be purified by reversed phase chromatography or the like to provide a nucleic acid probe for use in the present invention. For the introduction of the amino group, it is convenient to use a kit reagent [for example, "Unilink Aminomodifier" (trade name, product of Clontech Laboratories, Inc., Palo Alto, Calif. U.S.A.), or "FluoReporter Kit F-6082, F-6083, F-6084 or F-10220" (trade name, product of Molecular Probes, Inc.)]. In a manner known per se in the art, molecules of the fluorescent dye can then be conjugated to the oligoribonucleotide. It is also possible to introduce molecules of the fluorescent dye into strands of the probe nucleic acid (ANALYTICAL BIOCHEMISTRY, 225, 32–38, 1998).

The nucleic acid probe according to the present invention can be prepared as described above. A preferred probe form is one labeled with a fluorescent dye at the 3' or 5'end and containing G or C as the base at the labeled end. If the 5'end is labeled and the 3'end is not labeled, the OH group on the C atom at the 3'-position of the 3'end ribose or deoxyribose may be modified with a phosphate group or the like although no limitation is imposed in this respect.

Use of the nucleic probe according to the present invention is not limited to the determination of a nucleic acid, but it can also be suitably applied to methods for analyzing or determining polymorphism or mutation of a target nucleic acid or gene. In particular, its combined use with a DNA chip to be described subsequently herein provides a convenient method. Described specifically, the intensity of fluorescence upon hybridization of the nucleic acid probe of this invention with the target nucleic acid or gene varies depending on whether or not a GC pair is formed. It is, therefore, possible to analyze or determine polymorphism and/or mutation of a target nucleic acid or gene by hybridizing the nucleic acid probe according to the present invention to the target nucleic acid or gene and then measuring the intensity of emission. Specific methods will be described in Examples. In this case, the target nucleic acid or gene can be an amplified or extracted product obtained by desired one of nucleic acid or gene amplification or extraction methods. Further, no particular limitation is imposed on the kind of the target nucleic acid. Examples of the target nucleic acid to which the present invention is applicable can include RNAS, DNAS, PNAS, and artificially-modified nucleic acids. They are however required to contain a guanine base in strands thereof or at ends thereof, because the intensity of fluorescence would otherwise not decrease. The method of the present invention can, therefore, analyze or determine a mutation or substitution such as G→A, G←A, C→T, C←T, G→C or G←C, specifically, polymorphism such as single nucleotide polymorphism (SNP). Incidentally, it is the current practice to perform an analysis of polymorphism by determining the base sequence of a nucleic acid or gene in accordance with the Maxam-Gilbert method or the dideoxy method.

Inclusion of the nucleic acid probe according to the present invention in a kit for analyzing or determining polymorphism and/or mutation of a target nucleic acid or gene, therefore, makes it possible to suitably use the kit as a kit for the analysis or determination of the polymorphism and/or mutation of the target nucleic acid or gene.

When analyzing data obtained by the method of the present invention for the analysis or determination of polymorphism and/or mutation of a target gene, a processing step may be added to correct the intensity of fluorescence, which is emitted from the reaction system when the target nucleic acid has hybridized to the nucleic acid probe labeled with the fluorescent dye, by the intensity of fluorescence emitted from the reaction system when the target nucleic acid and the nucleic acid probe have not hybridized with each other. The data so processed are provided with high reliability. Accordingly, the present invention also provides a data analysis method for the method which analyzes or measures polymorphism and/or mutation of the target nucleic acid or gene.

The present invention also features a system for analyzing or determining polymorphism and/or mutation of a target nucleic acid or gene, which processing means for correcting a fluorescence intensity of a reaction system, in which the target nucleic acid or gene has hybridized to the nucleic acid probe labeled with the fluorescent dye, in accordance with a fluorescence intensity of the reaction system in which the target nucleic acid or gene has not hybridized to the nucleic acid probe labeled with the fluorescent dye.

The present invention further features a computer-readable recording medium with a program recorded therein for making a computer perform a processing step in which, when analyzing data obtained by the method for analyzing or determining polymorphism and/or mutation of a target nucleic acid or gene, a fluorescence intensity of a reaction system, in which the target nucleic acid or gene has hybridized to the nucleic acid probe labeled with the fluorescent dye, is corrected in accordance with a fluorescence intensity of the reaction system in which the target nucleic acid or gene has not hybridized to the nucleic acid probe labeled with the fluorescent dye.

The probe according to the present invention may be immobilized on a surface of a solid (support layer), for example, on a surface of a slide glass. In this case, the probe may preferably be immobilized on the end not labeled with the fluorescent dye. The probe of this form is now called a "DNA chips". These DNA chips can be used for monitoring gene expressions, determining base sequences, analyzing mutations or analyzing polymorphisms such as single nucleotide polymorphism (SNP). Needless to day, they can also be used as devices (chips) for determining nucleic acids.

To bind the probe of the present invention, for example, to a surface of a slide glass, a slide glass coated with polycations such as polylysine, polyethyleneimine or polyalkylamine, a slide glass with aldehyde groups introduced thereon, or a slide glass with amino groups introduced thereon is first provided. Binding can then be achieved, for example, by i) reacting phosphate groups of the probe to the slide glass coated with the polycations, ii) reacting a probe, in which amino groups have been introduced, to the slide glass on which aldehyde groups have been introduced or iii) reacting a probe, in which PDC (pyridinium dichlomate) residual groups, amino groups or aldehyde groups have been introduced, to the slide glass on which amino groups have been introduced (Fodor, P. A., et al., Science, 251, 767–773, 1991; Schena, W., et al., Proc. Natl. Acad. Sci., U.S.A., 93, 10614–10619, 1996; McGal, G., et al., Proc. Natl. Acad. Sci., U.S.A., 93, 13555–13560, 1996; Blanchad, A. P., et al., Biosens. Bioelectron., 11, 687–690, 1996).

A device having nucleic acid probes arranged and bound in an array form on a surface of a solid support permits more convenient determination of a nucleic acid.

In this case, formation of a device by individually binding many probes of this invention, the base sequences of which are different, on a surface of the same solid support makes it possible to simultaneously detect and quantitate a variety of genes.

Preferably, this device may be designed such that each probe is provided on a side of the solid support, said side being opposite to the side to which the probe is bound, with at least one temperature sensor and at least one heater and an area of the solid support, where the probe is bound, can be controlled to meet optimal temperature conditions.

For this device, probes other than those of the present invention, for example, nucleic acid probes of a construction designed such that two different fluorescent dyes are contained per molecule and each of the probes either quenches or emits fluorescence owing to interaction between the two fluorescent dyes when the probe is not hybridized with its corresponding target nucleic acid but either emits fluorescence or quenches when the probe hybridizes to the target nucleic acid, specifically, a device with molecular beacons described above (Tyagi et al., Nature Biotech., 14, 303–308, 1996) or the like bound thereon can also be used suitably. These devices, therefore, are embraced within the technical scope of the present invention.

Fundamental operations in the determination method making use of the device according to the present invention are simply to place a solution, which contains a target nucleic acid such as mRNA, cDNA or rRNA, on the solid support support on which the nucleic probes are bound and then to induce hybridization. As a result, a change in the intensity of fluorescence takes place corresponding to the concentration of the target nucleic acid, and the target nucleic acid can then be detected and quantitated from the change in the intensity of fluorescence. Further, binding of many nucleic acid probes of different base sequences on a surface of a single support makes it possible to detect and quantitate many nucleic acids at the same time. As this device can be used for exactly the same application as a DNA chip, it is a novel DNA chip. Under reaction conditions optimal for the target nucleic acid, the intensities of fluorescence emitted from the nucleic acids other than the target nucleic acid remain unchanged. No operation is, therefore, needed for washing off the unreacted nucleic acids. Further, independent temperature control of the individual nucleic acid probes by their corresponding microheaters makes it possible to control the probes under their optimal reaction conditions, respectively. Accurate quantitation is therefore feasible. In addition, a dissociation curve between each nucleic acid probe and its corresponding target nucleic acid can be analyzed by continuously changing the temperature with the microheater and measuring the intensity of fluorescence during the changing of the temperature. From differences in such dissociation curves, it is possible to determine properties of the hybridized nucleic acid and also to detect SNP.

According to each conventional device for determining a concentrations of a target nucleic acid, a nucleic acid probe not modified with a fluorescent dye is bound or fixed on a surface of a solid support and, subsequent to hybridization with the target nucleic acid labeled with the fluorescent dye, an unhybridized portion of the target nucleic acid is washed off, followed by the measurement of the intensity of fluorescence from the remaining fluorescent dye.

To label the target nucleic acid with the fluorescent dye, the following steps can be followed, for example, when specific mRNA is chosen as a target: (1) mRNA extracted from cells is extracted in its entirety, and (2) using a reverse transcriptase, cDNA is synthesized while inserting a nucleoside modified by the fluorescent dye. These operations are not needed in the present invention.

A number of various probes are applied in spots on the device. Optimal hybridization conditions, for example, temperatures or the like for nucleic acids to be hybridized to the individual probes are different from each other. Theoretically speaking, it is therefore necessary to conduct a hybridization reaction and a washing operation under optimal conditions for each probe (at each spot). This is however physically impossible. For all the probes, hybridization is conducted at the same temperature and further, washing is also carried out at the same temperature with the same washing solution. The device is, therefore, accompanied by a drawback that a nucleic acid does not hybridize although its hybridization is desired or that, even if its hybridization takes place, the nucleic acid is readily washed off as the hybridization is not strong. For these reasons, the accuracy of quantitation of the nucleic acid is low. The present invention does not have such a drawback because the above-mentioned washing operation is not needed. Further, a hybridization reaction can be conducted at an optimal temperature for each probe by independently arranging a microheater at the bottom of each spot and controlling the hybridization temperature. Accordingly, the accuracy of quantitation has been significantly improved in the present invention.

In the present invention, use of the above-described nucleic acid probe or device makes it possible to specifically determine a concentration of a target nucleic acid with ease in a short time.

A description will hereinafter be made of the determination method.

In the determination method according to the present invention, the above-described nucleic acid probe is added to a measurement system and is caused to hybridize to a target nucleic acid. This hybridization can be effected by a conventionally-known method (Analytical Biochemistry, 183, 231–244, 1999; Nature Biotechnology, 14, 303–308, 1996; Applied and Environmental Microbiology, 63, 1143–1147, 1997). As conditions for hybridization, the salt concentration may range from 0 to 2 molar concentration, preferably from 0.1 to 1.0 molar concentration, and the pH may range from 6 to 8, preferably from 6.5 to 7.5.

The reaction temperature may preferably be in a range of the Tm value of the hybrid complex, which is to be formed by hybridization of the nucleic acid probe to the specific site of the target nucleic acid, ±10° C. This temperature range can prevent non-specific hybridization. A reaction temperature lower than Tm−10° C. allows non-specific hybridization, while a reaction temperature higher than Tm+10° C. allows no hybridization. Incidentally, a Tm value can be determined in a similar manner as in an experiment which is needed to design the nucleic acid probe for use in the present invention. Described specifically, an oligonucleotide which is to be hybridized with the nucleic acid probe and has a complementary base sequence to the nucleic acid probe is chemically synthesized by the above-described nucleic acid synthesizer or the like, and the Tm value of a hybrid complex between the oligonucleotide and the nucleic acid probe is then measured by a conventional method.

The reaction time may range from 1 second to 180 minutes, preferably from 5 seconds to 90 minutes. If the reaction time is shorter than 1 second, a substantial portion of the nucleic acid probe according to the present invention remains unreacted in the hybridization. On the other hand, no particular advantage can be brought about even if the reaction time is set excessively long. The reaction time varies considerably depending on the kind of the nucleic acid, namely, the length or base sequence of the nucleic acid.

In the present invention, the nucleic acid probe is hybridized to the target nucleic acid as described above. The intensity of fluorescence emitted from the fluorescent dye is measured both before and after the hybridization, and a decrease in fluorescence intensity after the hybridization is then calculated. As the decrease is proportional to the concentration of the target nucleic acid, the concentration of the target nucleic acid can be determined.

The concentration of the target nucleic acid in the reaction mixture may range from 0.1 to 10.0 nM, while the concentration of the probe in the reaction mixture may range from 1.0 to 25.0 nM. Upon preparation of a working curve, the probe may desirably be used at ratios of from 1.0 to 2.5 relative to the target nucleic acid.

Upon actually determining the concentration of a target nucleic acid, the concentration of which is unknown, in a sample, a working curve is first prepared under the below-described conditions. A corresponding probe is added at plural concentrations to aliquots of the sample, respectively, followed by the measurement of decreases in fluorescence intensity. The probe concentration, which corresponds to the greatest one of the decreases in fluorescence intensity so measured, is chosen as a preferred probe concentration. Based on the decrease in fluorescence intensity measured at the preferred probe concentration, a quantitated value of the target nucleic acid can be determined from the working curve.

A description has been made about the principle of the method of the present invention for the determination of a concentration of a nucleic acid. The present invention can be applied to various nucleic acid determination methods, for example, fluorescent in situ hybridization assays, PCR methods, ligase chain reactions, strand displacement assays, competitive hybridizations, and TAS methods led by the NASBA method.

Examples of these applications will hereinafter be described.

a) Application to Fluorescent in situ Hybridization Assays

The present invention can be suitably applied to the determination of the concentration of a nucleic acid in cells of a cultivation system of microorganisms (e.g., a co-cultivation system of microorganisms or a symbiotic cultivation system of microorganisms), in which various kinds of microorganisms are contained together or a microorganism and other animal- or plant-derived cells are contained together and cannot be isolated from each other, or in a homogenate or the like of the cells of the cultivation system. The term "microorganisms" as used herein means microorganisms in general sense, and no particular limitation is imposed thereon. Examples of such microorganisms can include eukaryotic microorganisms and prokaryotic microorganisms, and also mycoplasmas, virus and rickettsias. The term "a nucleic acid having a specific sequence" means a nucleic acid with a base sequence specific to cells of a cell strain which is desired to be investigated, for example, as to how it is acting in such a microorganism. Illustrative examples can include 5S rRNAs, 16S rRNAs and 23S rRNAs of certain specific cell strains and particular sequences of their gene DNAS.

According to the present invention, a nucleic acid probe is added to a co-cultivation system of microorganisms or a symbiotic cultivation system of microorganisms and the concentration of 5S rRNA, 16S rRNA or 23S rRNA of a parituclar cell strain or its gene DNA, thereby making it possible to determine the viable count of the particular strain in the system. Incidentally, a viable count of a particular cell strain in a co-cultivation system of microorganisms or a symbiotic cultivation system of microorganisms can be determine by adding the nucleic acid probe to a homogenate of the system and then measuring a decrease in fluorescence emission from the fluorescent dye before hybridization relative to fluorescence emission from the fluorescent dye after the hybridization. It is to be noted that this method also falls within the technical scope of the present invention.

The above-described determination method can be carried out as will be described hereinafter. Before the addition of the nucleic acid probe, the temperature, salt concentration and pH of the co-cultivation system of microorganisms or the symbiotic cultivation system of microorganisms are adjusted to meet the conditions described above. It is also preferable to adjust the concentration of the specific cell strain, which is contained in the co-cultivation system of microorganisms or the symbiotic cultivation system of microorganisms, to $10^7$ to $10^{12}$ cells/mL, preferably $10^9$ to $10^{10}$ cells/mL in terms of viable count. These adjustments can be achieved by dilution, centrifugal or like concentration, or the like. A viable count smaller than $10^7$ cells/mL results in low fluorescence intensity and greater determination error. A viable count greater than $10^{12}$ cells/mL, on the other hand, leads to excessively high fluorescence intensity, so that the viable count of the particular microorganism cannot be determined quantitatively.

The concentration of the nucleic acid probe to be added depends upon the viable count of the particular cell strain in the co-cultivation system of microorganisms or the symbiotic cultivation system of microorganisms and, at a viable count of $10^8$ cells/mL, maybe in a range of from 0.1 to 10.0 nM, preferably in a range of from 0.5 to 5 nM, more preferably 1.0 nM. A probe concentration lower than 0.1 nM cannot provide any data which accurately reflects the viable count of the particular microorganism. The probe concentration, however, cannot be specified in any wholesale manner because it depends upon the concentration of a target nucleic acid in cells.

Upon hybridizing the nucleic acid probe to the 5S rRMA, 16S rRNA or 23S rRNA of the particular cell strain or its gene DNA in the present invention, the reaction temperature may be set as described above. Further, the hybridization time may also be set as described above.

The nucleic acid probe is hybridized to the 5S rRNA, 16S rRNA or 23S rRNA of the particular cell strain or its gene DNA under such conditions as described above. A decrease in fluorescence emission from the fluorescent dye in the co-cultivation system of microorganisms or the symbiotic cultivation system of microorganisms before the hybridization relative to the corresponding fluorescence emission before the hybridization is then determined.

The decrease in fluorescence emission from the florescent dye, which is determined as described above, is proportional to the viable count of the particular cell strain in the co-cultivation system of microorganisms or the symbiotic cultivation system of microorganisms, because the concentration of the 5S rRMA, 16S rRNA or 23S rRNA or its gene DNA and the viable count of the particular cell strain are proportional to each other.

In the present invention, no particular limitation is imposed on components other than the microorganisms in the co-cultivation system of microorganisms or the symbiotic cultivation system of microorganisms, insofar as the components do not interfere with the hybridization between the nucleic acid probe according to the present invention and the 5S rRNA, 16S rRNA or 23S rRNA or its gene DNA and further, do not inhibit emission of fluorescence from the fluorescent dye in the nucleic acid probe. For example, phosphates such as $KH_2PO_4$, $K_2HPO_4$, $NaH_2PO_4$ and $Na_3HPO_4$, inorganic nitrogen compounds such as ammonium sulfate, ammonium nitrate and urea, various salts of metal ions such as magnesium, sodium, potassium and calcium ions, various salts such as the sulfates, hydrochlorides, carbonates and the like of trace metal ions such as magnesium, zinc, iron and cobalt ions, and vitamins may be contained to adequate extent. If the above-described interference or inhibition is observed, it may be necessary to separate cells of the plural microorganisms from the cultivation system by an operation such as centrifugal separation and then to resuspend them in a buffer or the like.

Usable examples of the buffer can include various buffers such as phosphate buffer, carbonate buffer, Tris-HCl buffer, Tris-glycine buffer, citrate buffer, and Good's buffer. The buffer should be adjusted to a concentration not inhibiting the hybridization, the FRET phenomenon or the emission of fluorescence from the fluorescent dye. This concentration depends upon the kind of the buffer, The pH of the buffer may range from 4 to 12, with 5 to 9 being preferred.

b) Application to PCR Methods

The present invention can be applied to any method insofar as it is a PCR method. A description will hereinafter be made of an application of the present invention to a real-time quantitative PCR method.

In the real-time quantitative PCR method, PCR is conducted using a specific nucleic acid probe according to the present invention, and a decrease in fluorescence emission from the florescent dye before a reaction relative to fluorescence emission from the fluorescent dye after the reaction is determined in real time.

The term "PCR" as used herein means a variety of PCR methods. Examples can include RT-PCR, RNA-primed PCR, stretch PCR, reverse PCR, PCR making use of an Alu sequence, multiple PCR, PCR making use of a mixed primer, and PCR making use of PNA. Further, the term "quantitative" means, in addition to quantitation in general sense, quantitation of such an extent as detection.

As described above, the term "target nucleic acid" as used herein means a nucleic acid the quantitation or qualitative detection or mere detection of which is intended, irrespective whether it is in a purified form or not and further irrespective of its concentration. Various other nucleic acids may also exist together with the target nucleic acid. For example, the target nucleic acid may be a specific nucleic acid in a co-cultivation system microorganisms (a mixed system of RNAs or gene DNAs of plural microorganisms) or a symbiotic cultivation system of microorganisms (a mixed system of RNAs or gene DNAs of plural animals, plants and/or microorganisms), the amplification of which is intended. Purification of the target nucleic acid, if needed, can be conducted by a method known per se in the art. For example, purification can be effected using a purification kit or the like available on the market.

The conventionally-known quantitative PCR methods individually amplify, in the presence of Mg ions, a target nucleic acid by using dATP, dGTP, dCTP, dTTP or dUTP, a target nucleic acid (DNA or RNA), Taq polymerase, a primer, and a nucleic acid labeled with a fluorescent dye or an intercalator while repeatedly changing the temperature between low and high levels, and monitor increases in fluorescence emission from the fluorescent dye in real time in the course of the amplification [Jikken Igaku (Laboratory Medicine), 15(7), 46–51, Yodosha (1997)].

On the other hand, the quantitative PCR method according to the present invention is characterized in that the target nucleic acid is amplified by using the nucleic probe of the present invention and a decrease in fluorescence emission from the fluorescent dye is determined. The number of bases in a preferred probe of the present invention for use in the quantitative PCR according to the present invention may be from 5 to 50, preferably from 10 to 25, notably from 15 to 20. No particular limitation is imposed on the probe insofar as it hybridizes to amplification products of the target nucleic acid in PCR cycles. The probe may be designed in either a forward type or a reverse type.

The followings can be mentioned as illustrative examples:

(1) A probe labeled, at a 5'end portion, preferably, the 5'end thereof, with a fluorescent dye useful in the practice of the present invention. The base sequence of the probe is designed such that, when hybridized at the end portion with a target nucleic acid, at least one G (guanine) base exists in the base sequence of the target nucleic acid at a position 1 to 3 bases apart toward the 5' side from the base on the 5'end at which the probe and the target nucleic acid are hybridized with each other.

(2) A probe similar to the probe (1) except that the 3'end is labeled with the fluorescent dye.

(3) A probe similar to the probe (1) except that the 3'end, for example, the OH group on the C atom at the 3'-position of ribose or deoxyribose at the 3'end has been modified by a phosphate group or the like or that the OH group at the 2'-position of ribose at the 3'end has been modified by a phosphate group or the like.

(4) A probe labeled at the 3'end portion, preferably the 3'end with the fluorescent dye useful in the practice of the present invention and containing G or C as a base at the 3'end.

(5) A probe similar to the probe (1) except that the 5'end portion, preferably, the 5'end is labeled with the fluorescent dye useful in the practice of the present invention.

(6) A probe labeled at the 5'end portion, preferably the 5'end with the fluorescent dye useful in the practice of the present invention and containing G or C as a base at the 5'end.

In the case of each of the probes (4),(6), the 5'end may not be designed to G or C due to the base sequence of a target nucleic acid. If this should be the case, 5'-guanylic acid or 5'-cytidylic acid may be added to the 5'end of an oligonucleotide designed as a primer from the base sequence of the target nucleic acid. The probe so obtained can still achieve the objects of the present invention adequately. The expression "nucleic acid probe designed such that the 3'end or 5'end base thereof becomes G or C" as used herein is, therefore, defined to embrace not only probes designed based on the base sequence of the target nucleic acid but also probes added at the 3'end or 5'end thereof with 5'-guanylic acid or 5'-cytidylic acid.

In particular, the above-described probe (1), (2), (3) or (4) is designed such that it is not used as a primer. PCR is conducted by using a single probe of the present invention as opposed to two (fluorescent-dye-labeled) probes needed in a real-time quantitative PCR method making use of the FRET phenomenon. The probe is added to a PCR reaction system, and PCR is then conducted. During a nucleic acid extending reaction, the probe which has been in a form hybridized with the target nucleic acid or amplified target nucleic acid is degraded by polymerase and is dissociated off from the hybrid complex. The intensity of fluorescence of the reaction system at this time or the reaction system in which a nucleic acid denaturing reaction has completed is measured. Further, the intensity of fluorescence of the reaction system in which the target nucleic acid or amplified target nucleic acid has hybridized with the probe (i.e., the reaction system at the time of an annealing reaction or at the time of the nucleic acid extending reaction until the probe is eliminated from the hybrid complex by polymerase). By calculating a decrease of the latter fluorescence intensity from the former fluorescence intensity, the concentration of the amplified nucleic acid is determined. The intensity of fluorescence is high when the probe has completely dissociated from the target nucleic acid or amplified target nucleic acid by the nucleic acid denaturing reaction or when the probe has been degraded out from the hybrid complex of the probe and the target nucleic acid or amplified nucleic acid at the time of extension of the nucleic acid. However, the intensity of fluorescence of the reaction system in which an annealing reaction has been completed and the probe has fully hybridized to the target nucleic acid or amplified target nucleic acid or of the reaction system until the probe is degraded out of the hybrid complex of the probe and the target nucleic acid or amplified target nucleic acid by polymerase at the time of a nucleic acid extending reaction is lower than the former. The decrease in the intensity of fluorescence is proportional to the concentration of the amplified nucleic acid.

In this case, each of the base sequences of the probes (2), (3), (4) may desirably be designed such that the Tm of a hybrid complex, which is available upon hybridization of the probe with the target nucleic acid, falls within a range of the Tm value of the hybrid complex of the primer ±15° C., preferably ±5° C. If the Tm of the probe is lower than (the Tm value of the primer –5° C.), especially (the Tm value of the primer –15° C.), the probe does not hybridize so that no decrease takes place in the fluorescence emission from the fluorescent dye. If the Tm of the probe is higher than (the Tm value of the primer+5° C.), especially (the Tm value of the primer+15° C.), the probe also hybridizes to nucleic acid or acids other than the target nucleic acid so that the specificity of the probe is lost.

The probes (5), (6) are added as primers to PCR reaction systems. Except for the PCR method according to the present invention, no PCR method is known to make use of a primer labeled with a fluorescent dye. As the PCR reaction proceeds, the amplified nucleic acid is progressively labeled with the fluorescent dye useful in the practice of the present invention. Accordingly, the intensity of fluorescence of the reaction system in which the nucleic acid denaturing reaction has completed is high but, in the reaction system in which the annealing reaction has completed or the nucleic acid extending reaction is proceeding, the intensity of fluorescence of the reaction system is lower than the former intensity of fluorescence.

The PCR reaction can be conducted under similar conditions as in conventional PCR methods. It is, therefore, possible to conduct amplification of a target nucleic acid in a reaction system the concentration of Mg ions in which is low (1 to 2 mM). Needless to say, the present invention can also be conducted even in a reaction system in which Mg ions are contained at such a high concentration (2 to 4 mM) as that employed in the conventionally-known quantitative PCR methods.

In the PCR method according to the present invention, Tm value can be determined by conducting the PCR of the present invention and then analyzing the melting curve of the nucleic acid with respect to the amplification products. This method is a novel analysis method of a melting curve of a nucleic acid. In this method, the nucleic acid probe employed as a nucleic acid probe or primer in the PCR method of the present invention can be used suitably.

In this case, designing of the base sequence of the probe according to the present invention into a sequence complementary with a.region containing SNP (single nucleotide polymorphism) makes it possible to detect SNP from a difference, if any, in a dissociation curve of the nucleic acid from the probe of the present invention by analyzing the dissociation curve after completion of PCR. If a base sequence complementary with an SNP-containing sequence is used as a sequence for the probe of the present invention, a Tm value available from a dissociation curve between the sequence of the probe and the SNP-containing sequence becomes higher than a TM value available from a dissociation curve between the sequence of the probe and the SNP-free sequence.

A second feature of the present invention resides in the method for analyzing data obtained by the above-described real-time quantitative PCR method.

A real-time quantitative PCR method is now practiced in real time by a system which is composed of a reactor for conducting PCR, an equipment for detecting fluorescence emission from a fluorescent dye, a user interface, namely, a computer-readable recording medium with various procedures of a data analysis method recorded as a program (also called "sequence detection software system), and a computer for controlling them and analyzing data. Determination by the present invention is also conducted by such a system.

A description will first be made of an analyzer for real-time quantitative PCR. Any system can be used in the present invention insofar as it can monitor PCR in real time. Particularly suitable examples can include "ABI PRISM™ 7700 Sequence Detection System (SDS 7700)" (manufactured by Perkin-Elmer Applied Biosystems, Inc., U.S.A.) and "LightCycler™ System" (manufactured by Roche Diagnostics, Mannheim, Germany).

The above-described reactor is an apparatus for repeatedly conducting a thermal denaturing reaction of a target nucleic acid, an annealing reaction and an extending reaction of the nucleic acid (these reactions can be repeatedly conducted, for example, by successively changing the temperature to 95° C., 60° C. and 72° C. The detection system comprises a fluorescence emitting argon laser, a spectrograph and a CCD camera. Further, the computer-readable recording medium with the various procedures of the data analysis method recorded as the program is used by installing it in the computer, and contains a program recorded therein for controlling the above-described system via the computer and also for processing and analyzing data outputted from the detection system.

The data analysis program recorded in the computer-readable recording medium comprises the following steps: measuring the intensity of fluorescence cycle by cycle, displaying each measured fluorescence intensity as a function of cycles, namely, as a PCR amplification plot on a display of the computer, calculating a threshold cyclenumber (Ct) at which the intensity of fluorescence is begun to be detected, forming a working line useful in determining from Ct values the number of copies of the nucleic acid in the sample, and printing data and plot values in the respective steps. When PCR is exponentially proceeding, a linear relationship is established between the logarithm of the number of copies of the targent nucleic acid at the time of initiation of PCR and Ct. It is therefore possible to calculate the number of copies of the target nucleic acid at the time of initiation of PCR by forming a working line based on known copy numbers of the target nucleic acid and detecting the Ct of a sample which contains the target nucleic acid the number of copies of which is unknown.

The PCR-related invention is an invention for analyzing data obtained by such a real-time quantitative PCR method as described above. Its respective features will be described hereinafter.

A first feature resides in a processing step for correcting a fluorescence intensity of a reaction system, which is measured when the nucleic acid amplified in each cycle is conjugated with the fluorescent dye or when the amplified nucleic acid hybridizes to a nucleic acid probe labeled with the fluorescent dye in the method for analyzing data obtained by the real-time quantitative PCR method, by a fluorescence intensity of the reaction system as obtained when the above-described conjugate or hybrid complex has dissociated in each cycle, namely, the first feature resides in a correction-processing step.

As a specific example of "the reaction system . . . when the nucleic acid amplified in each cycle is conjugated with the fluorescent dye or when the amplified nucleic acid hybridizes to a nucleic acid probe labeled with the fluorescent dye", a reaction system upon conducting a nucleic acid extending reaction or annealing at 40 to 85° C., preferably 50 to 80° C. in each cycle of PCR can be mentioned. The actual temperature depends upon the length of the amplified nucleic acid.

Further, "the reaction system . . . when the above-described conjugate or hybrid complex has dissociated" can be a reaction system upon conducting thermal denaturation of the nucleic acid in each cycle of PCR, specifically at a reaction temperature of from 90 to 100° C., preferably 94 to 96° C.

Any correction processing can be used as the correction processing in the correction processing step insofar as it conforms with the objects of the present invention. Specifically, correction processing including a processing step by the following formula (1) or formula (2) can be exemplified.

$$f_n = f_{hyb,n} / f_{den,n} \tag{1}$$

$$f_n = f_{den,n} / f_{hyb,n} \tag{2}$$

where $f_n$: correction-processed value in an $n^{th}$ cycle as calculated in accordance with the formula (1) or formula (2), $f_{hyb,n}$: intensity value of fluorescence of the reaction system available after the amplified nucleic acid has conjugated to the fluorescent dye or the amplified nucleic acid has hybridized to the nucleic acid probe labeled with the fluorescent dye in the $n^{th}$ cycle, and $f_{den,n}$: intensity value of fluorescence of the reaction system available after the nucleic acid-fluorescent dye conjugate has dissociated in the $n^{th}$ cycle.

This step includes a sub-step in which correction-processed values obtained by the above-described processing are displayed on a computer display and/or are printed or the correction-processed values are likewise displayed and/or printed in the form of a graph as a function of cycles.

A second feature resides in a data analysis method, which comprises:

introducing correction-processed values, which have been calculated in accordance with the formula (1) or formula (2) in individual cycles, into the following formula (3) or formula (4) to calculate rates or percentages of changes in fluorescence between samples in the individual cycles:

$$F_n = f_n / f_a \tag{3}$$

$$F_n = f_a / f_n \tag{4}$$

where $F_n$: rate or percentage of a change in fluorescence in an $n^{th}$ cycle as calculated in accordance with the formula (3) or formula (4), $f_n$: correction-processed value calculated in the $n^{th}$ cycle as calculated in accordance with the formula (1) or formula (2), and $f_a$: correction-processed value calculated in a given cycle before a change in $f_n$ is observed as calculated in accordance with the formula (1) or formula (2), and in general, a correction-processed value, for example, in one of $10^{th}$ to $40^{th}$ cycles, preferably one of $15^{th}$ to $30^{th}$ cycles, more preferably one of $20^{th}$ to $30^{th}$ cycles is adopted; and comparing the rates or percentages of changes in fluorescence.

This step includes a sub-step in which calculated values obtained by the above-described processing are displayed on a computer display and/or are printed or the calculated values are likewise displayed and/or printed in the form of a graph as a function of cycles. This sub-step may be applied or may not be applied to the correction-processed values obtained by the formula (1) or formula (2).

A third feature resides in a data analysis method, which comprises the following processing steps:

1) performing processing in accordance with the following formula (5), (6) or (7) by using data of rates or percentages of changes in fluorescence as calculated in accordance with said formula (3) or (4):

$$\log_b(F_n), \ln(F_n) \quad (5)$$

$$\log_b\{(1-F_n) \times A\}, \ln\{(1-F_n) \times A\} \quad (6)$$

$$\log_b\{(F_n-1) \times A\}, \ln\{(F_n-1) \times A\} \quad (7)$$

where

A,b: desired numerical values, preferably integers, more preferably natural numbers and, when A=100, b=10, $\{(F_n-1) \times A\}$ is expressed in terms of percentage (%), and $F_n$: rate or percentage of a change in fluorescence in an $n^{th}$ cycle as calculated in accordance with the formula (3) or formula (4), 2) determining a cycle in which said processed value of said processing step 1) has reached a constant value, 3) calculating a relational expression between cycle of a nucleic acid sample of a known concentration and the number of copies of said target nucleic acid at the time of initiation of a reaction, and 4) determining the number of copies of said target nucleic acid in an unknown sample upon initiation of PCR.

Preferably, these steps are performed in the order of 1)→2)→3)→4).

Each of these steps 1) to 3) includes a sub-step in which processed values obtained by the corresponding processing are displayed on a computer display and/or are printed or the processed values are likewise displayed and/or printed in the form of a graph as a function of cycles. The step 4) should include at least a printing sub-step as the processed values obtained in the step 4) have to be printed, although the processed values obtained in the step 4) may also displayed on a computer display.

Incidentally, the correction-processed values obtained by the formula (1) or (2) and the calculated values obtained by the formula (3) or (4) may be or may not be displayed on a computer display and/or printed in the form of graphs as a function of cycles, respectively. These displaying and/or printing sub-steps may, therefore, be added as needed.

The above-described data analysis method is particularly effective when decreases in fluorescence emission from the fluorescent dye are measured in the real-time quantitative PCR method. As a specific example, the real-time quantitative PCR method according to the present invention can be mentioned.

A fourth feature resides in an analysis system for real-time quantitative PCR, which comprises processing and storing means for performing a data analysis method for the above-described real-time quantitative PCR method of the present invention.

A fifth feature resides in a computer-readable recording medium with individual procedures of a data analysis method, which is adapted to analyze PCR by using the analysis sytem for the real-time quantitative PCR, stored as a program therein, wherein the program is designed to make a computer perform the individual procedures of the data analysis method of the present invention.

A sixth feature resides in a novel method for determining a nucleic acid, which comprises using the data analysis method, determination and/or analysis system and/or recording medium of the present invention in the nucleic acid determination method.

A seventh feature resides in a method for analyzing data obtained by the above-described method of the present invention for the analysis of a melting curve of a nucleic acid, namely, data obtained by the method of the present invention in which the Tm value of the nucleic acid is determined by conducting PCR.

Specifically, the seventh feature resides in an analysis method, which comprises the following steps: gradually heating a nucleic acid, which has been amplified by the PCR method of the present invention, from a low temperature until complete denaturation of the nucleic acid (for example, from 50° C. to 95° C.; measuring an intensity of fluorescence at short time intervals (for example, at intervals equivalent to a temperature rise of from 0.20° C. to 0.5° C.) during the heating step; displaying results of the measurement as a function of time on a display, namely, a melting curve of the nucleic acid; differentiating the melting curve to obtain differentiated values (−dF/dT, F: intensity of fluorescence, T: time); displaying the differentiated values as derivatives on the display; and determining a point of inflection from the derivatives. In the present invention, the intensity of fluorescence increases as the temperature rises. Preferable results can be obtained in the present invention by adding to the above-described step a further processing step in which in each cycle, the intensity of fluorescence at the time of the nucleic acid extending reaction, preferably at the time of completion of the PCR reaction is divided by the value of fluorescence intensity at the time of the thermal denaturing reaction.

A measurement and/or analysis system for the real-time quantitative PCR of the present invention, said real-time quantitative PCR including the method of the present invention for the analysis of the melting curve of a nucleic acid to the above-described novel method of the present invention for the analysis of data obtained by a PCR method, also falls within the technical scope of the present invention.

A still further feature of the present invention resides in a computer-readable recording medium with the individual procedures of the method of the present invention for the analysis of the melting curve of a nucleic acid recorded therein as a program such that the procedures can be performed by a computer or a computer-readable recording medium with the individual procedures of the method of the present invention for the analysis of data obtained by a PCR method recorded therein as a program such that the procedures can be performed by a computer, wherein a program designed to make the computer perform the individual procedures of the method of the present invention for the analysis of the melting curve of the nucleic acid is additionally recorded.

The above-described data analysis methods, systems and recording media of the present invention can be used in a variety of fields such as medicine, forensic medicine, anthropology, paleontology, biology, genetic engineering, molecular biology, agricultural science and phytobreeding.

They can be suitably applied to microorganism systems called "co-cultivation systems of microorganisms" or "symbiotic cultivation systems of microorganisms", in each of which various kinds of microorganisms are contained together or a microorganism and other animal- or plant-derived cells are contained together and cannot be isolated from each other. The term "microorganisms" as used herein means microorganisms in general sense, and no particular limitation shall be imposed thereon, Illustrative are eukaryotic microorganisms, prokaryotic microorganisms, mycoplasmas, virus and rickettsias.

The vial count of a particular cell strain in a co-cultivation system of microorganisms or a symbiotic cultivation systems of microorganisms can be determined by determining the number of copies of the 5S rRNA, 16S rRNA or 23S rRNA of the particular cell strain or its gene DNA in the system by using one or more of the above-described data analysis methods, systems and recording media of the present invention, because the number of copies of the gene DNA of 5S rRNA, 16S rRNA or 23S rRNA is specific to each cell strain. In the present invention, the vial count of a particular cell strain can also be determined by applying the real-time quantitative PCR of the present invention to a homogenate of a co-cultivation system of microorganisms or a symbiotic cultivation systems of microorganisms. It shall also be noted that this method also falls with the technical scope of the present invention.

The present invention will next be described more specifically based on the following Examples and Comparative Examples.

EXAMPLE 1

Preparation of a nucleic acid probe to be hybridized to the base sequence of a nucleic acid ranging from the 335$^{th}$ base to 358$^{th}$ base counted from the 5' end in 16S rRNA of *Escherichia coli*, namely, preparation of a nucleic acid probe having a base sequence of (3')CCGCTCACGCATC(5') was conducted as will be described hereinafter.

Preparation of Nucleic Acid Probe

A deoxyribooligonucleotide, which had the base sequence of (3')CCGCTCACGCATC(5') and contained —(CH$_2$)$_7$—NH$_2$ bonded to the OH group on the carbon atom at the 3' position of deoxyribose at the 3' end of the deoxyribooligonucleotide, was purchased from Midland Certified Reagent Company, U.S.A. From Molecular Probes, Inc., "FluoroReporter Kit F-6082" (trade name) was also purchased, which contained not only "BODIPY FL" propionic acid succinimidyl ester but also a reagent for conjugating the compound to the amine derivative of the oligonucleotide. The kit was caused to act on the above-purchased oligonucleotide, whereby a nucleic acid probe labeled with "BODIPY FL" was synthesized for use in this Example.

Purification of Synthesized Product

The synthesized product was dried into a dry product. The dry product was dissolved in 0.5 M NaHCO$_3$/Na$_2$CO$_3$ buffer (pH 9.0). The solution was subjected to gel filtration through "NAP-25 Column" (trade name, product of Pharmacia AB, Uppsala, Sweden), whereby unreacted substances were removed. Further, reversed phase UPLC (B gradient: 15 to 65%, 25 minutes) was conducted under the below-described conditions. An eluted main fraction was collected. The collected fraction was lyophilized, whereby a nucleic acid probe was obtained with a yield of 23% as calculated relative to 2 mM of the starting oligonucleotide.

The above-described reversed phase chromatography was conducted under the following conditions:

Eluting solvent A: 0.05 N TEAA 5% CH$_3$CN

Eluting solvent B (for gradient elution): 0.05 N TEAA 40% CH$_3$CN

Column: CAPCEL PAK C18 (trade name), 6×250 mm

Elution rate: 1.0 mL/min

Temperature: 40° C.

Detection: 254 nm

EXAMPLE 2

Using a 200-mL Erlenmeyer flask which contained sterilized nutrient broth (NB) (50 mL; product of Difco; composition: NB, 0.08 g/100 mL), *Escherichia coli* JM109 was cultured overnight at 37° C. under shaking. To the culture, an equivalent amount of 99.7% ethanol was then added. A 2-mL aliquot of the ethanol-added culture was centrifuged in a 2.0-mL Eppendorf centrifuge tube, whereby cells were obtained. The cells were washed once with 30 mM phosphate buffer (sodium salt) (100 μL; pH 7.2). The cells were suspended in the phosphate buffer (100 μL) which contained 130 mM NaCl. The suspension was ultrasonicated for 40 minutes under ice cooling (output: 33 W, oscillating frequency: 20 kHz, oscillation method: 0.5-second oscillation, followed by a 0.5-second pause), whereby a homogenate was prepared.

After the homogenate was centrifuged, the supernatant was collected and was then transferred into a cell of a fluorimeter. The cell with the supernatant placed therein was controlled at 36° C. A solution of the above-described nucleic acid probe, said solution having had been controlled to 36° C. beforehand, was added to the supernatant to give a final concentration of 5 nM. While controlling at 36° C., *E. coli* 16S rRNA and the nucleic acid probe were hybridized for 90 minutes. Intensity of fluorescence emission from the fluorescent dye was then measured by the fluorimeter.

Figure 1:
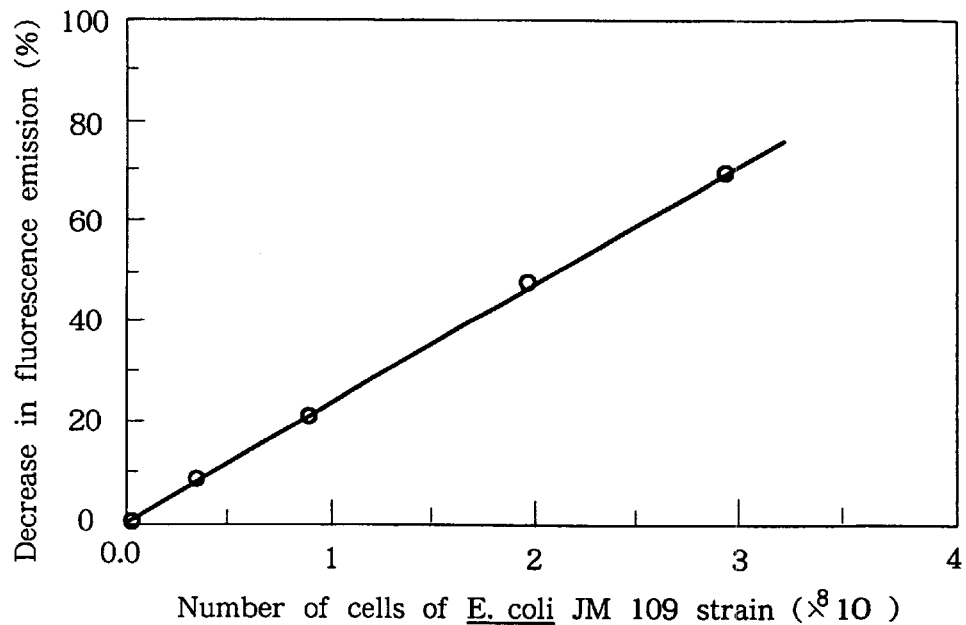
FIG. 1 is a diagram showing measurement data of fluorescence intensity when the sequence of bases in 16S rRNA of *Escherichia coli,* said bases ranging from the 335$^{th}$ base to the 358$^{th}$ base as counted from the 5'end, was determined using a nucleic acid probe obtained in Example 1.

As the intensity of fluorescence emission from the fluorescent dye before the hybridization, a value measured by using 30 mM phosphate buffer (sodium salt), which contained 130 mM NaCl, (pH: 7.2) instead of the above-described supernatant was adopted. Intensity of fluorescence emission was measured by changing the ratio of the amount of the nucleic probe to the amount of the supernatant (exciting light: 503 nm; measured fluorescence color.: 512 nm). The results are shown in FIG. 1. As is appreciated from FIG. 1, the intensity of fluorescence emission from the fluorescent dye decreased as the ratio of the amount of the supernatant increased. Namely, it is understood that in the present invention, the magnitude of a decrease in fluorescence emission from a fluorescent dye becomes greater in proportion to the amount of a target nucleic acid to which a nucleic acid probe hybridizes.

EXAMPLE 3

Preparation of Nucleic Acid Probe

An oligonucleotide, which was to be hybridized to 23S rNA of *Escherichia coli* JM109, had a base sequence of (5') CCCACATCGTTTTGTCTGGG (3') and contained —(CH$_2$)$_7$—NH$_2$ bonded to the OH group on the carbon atom at the 3' position of the 5' end nucleotide of the oligonucleotide, was purchased from Midland Certified Reagent Company, U.S.A. as in Example 1. From Molecular Probes, Inc., "FluoroReporter Kit F-6082" (trade name) was also purchased, which contained not only "BODIPY FL" propionic acid succinimidyl ester but also a reagent for conjugating the compound to the amine derivative of the oligonucleotide. The kit was caused to act on the above-purchased oligonucleotide, whereby a nucleic acid probe labeled with "BODITPY FL" was synthesized. The synthesized product so obtained was purified as in Example 1, whereby the nucleic acid probe labeled with "BODIPY FL" was obtained with a yield of 25% as calculated relative to 2 mM of the starting oligonucleotide.

EXAMPLE 4

With *Escherichia coli* JM109 cells obtained in Example 2, cells of *Psuedomonas paucimobilis* (now called "*Sphingomonag paucimobilis*) 421Y (FERM P-5122), said cells having have been obtained using the same culture medium and cultivation conditions as in Example 2, were mixed at the same concentration as *Escherichia coli* JM109 in terms of OD660 value, whereby a co-cultivation system of the microorganisms was prepared. From the resulting mixed system in which the cell concentration of *Escherichia coli* JM109 was the same as that in Example 2, a homogenate was prepared in the same manner as in Example 2. An experiment was conducted in a similar manner as in Example 2 except that the nucleic acid probe prepared in Example 3 was used, 543 nm exciting light was used, and 569 nm flourescence was measured. The results were similar to those obtaineed in Example 2.

EXAMPLE 5

The base selectivity of a target nucleic acid in the quenching phenomenon fluorescence, that is, the base selectivity according to the present invention was investigated. Ten kinds of synthetic dooxyribooligonucleotides (30 mer; poly a to poly j), which will be described subsequently herein, were prepared by a DNA synthesizer, "ABI394" (trade name; manufactured by Perkin-Elmer Corp.)

Also prepared were the below-described probes according to the present invention, which were labeled with "BODIPY FL" at the 5' ends of deoxyribooligonucleotides corresponding to the above-described synthetic DNAS, respectively.

Primer DNAs, which corresponded to the above-described synthetic DNAs and contained —(CH$_2$)$_8$—NH$_2$ bonded to the phosphate groups at the 5' ends of the primer DNAs, were purchased from Midland Certified Reagent Company. From Molecular Probes, Inc., "FluoroReporter Kit F-6082" (trade name) was also purchased, which contained not only "BODIPY FL" propionic acid succinimidyl ester but also a reagent for conjugating the compound to the amine derivative of the oligonucleotide. The kit was caused to act on the above-purchased primer DNAs, whereby invention nucleic acid probes labeled with "BODIPY FL" (probes a, b, c, d, f, g, h) were synthesized. An investigation was made under the below-described conditions to determine how much the fluorescence emission from the fluorescent dye would decrease when the probes were caused to hybridize to their corresponding synthetic deoxyribooligonucleotides, and the specificity of the invention probes was studied.

| Name | Target deoxyribooligonucleotide |
|---|---|
| poly a | 5'ATATATATTTTTTTGTTTTTTTTTTTTT3' |
| poly b | 5'ATATATATTTTTTTTGTTTTTTTTTTTTT3' |
| poly c | 5'ATATATATTTTTTTTTGTTTTTTTTTTT3' |
| poly d | 5'ATATATATTTTTTTTTTGTTTTTTTTTT3' |
| poly e | 5'ATATATATTTTTTTTTTTGTTTTTTTTT3' |
| poly f | 5'ATATATATTTTTTTTCTTTTTTTTTTTT3' |
| poly g | 5'ATATATATTTTTTTTTCTTTTTTTTTTT3' |

-continued

| Name | Target deoxyribooligonucleotide |
|---|---|
| poly h | 5'ATATATATTTTTTTTTTCTTTTTTTTTTT3' |
| poly i | 5'ATATATATTTTTTTTTTTCTTTTTTTTTT3' |
| poly j | 5'ATATATATTTTTTTTTTTTCTTTTTTTTT3' |

| Name | Invention probe |
|---|---|
| Probe a | 3'TATATATAAAAAAAACAA5'-BODIPY FL/C6 |
| Probe b | 3'TATATATAAAAAAAACA5'-BODIPY FL/C6 |
| Probe c | 3'TATATATAAAAAAAAAC5'-BODIPY FL/C6 |
| Probe d | 3'TATATATAAAAAAAAAA5'-BODIPY FL/C6 |
| Probe f | 3'TATATATAAAAAAAGAA5'-BODIPY FL/C6 |
| Probe g | 3'TATATATAAAAAAAAGA5'-BODIPY FL/C6 |
| Probe h | 3'TATATATAAAAAAAAAG5'-BODIPY FL/C6 |

(1) Components of hybridization mixture

| | |
|---|---|
| Synthetic DNA | 320 nM (final concentration) |
| Nucleic acid probe | 80 nM (final concentration) |
| NaCl | 50 nM (final concentration) |
| MgCl$_2$ | 1 nM (final concentration) |
| Tris-HCl buffer (pH 7.2) | 100 nM (final concentration) |
| "MiliQ" purified water | 1.6992 mL |
| Final whole volume | 2.0000 mL |

(2) Hybridization temperature: 51° C.
(3) Measuring conditions

Exciting light: 543 nm

Measured fluorescence color: 569 nm

TABLE 1

| Nucleic acid probe | Target nucleic acid | Decrease in Fluorescence intensity (%) |
|---|---|---|
| a | a | −10 |
| b | b | 2 |
| c | c | 75 |
| d | d | 48 |
| d | e | 18 |
| f | f | −8 |
| g | g | −2 |
| h | h | 70 |
| d | I | −6 |
| d | j | −5 |

The results are shown in Table 1. As is appreciated from Table 1, it is preferred to design the base sequence of a nucleic acid probe labeled with a fluorescent dye such that, when the nucleic acid probe is hybridized with a target DNA (deoxyribooligonucleotide), at least one G (guanine) base exists in the base sequence of the target DNA at a position 1 to 3 bases apart from an end base portion where the probe and the target DNA are hybridized with each other. From Table 1, it is also understood to be desired to design the base sequence of a nucleic acid probe labeled with a fluorescent dye such that, when the nucleic acid probe is hybridized with a target, base pairs in the probe-DNA hybrid complex form at least one G (guanine) and C (cytosine) pair at the end portion.

EXAMPLE 6

Target nucleic acids and invention nucleic acid probes of the below-described base sequences were prepared. In a similar manner as in the preceding Example, an investigation was made about effects of the number of G(s) in each target nucleic acid and the number of G(s) in its corresponding invention nucleic acid probe.

| Name | Target deoxyribooligonucleotide |
|---|---|
| poly k | 5'TATATATATATTTTTGGGGG3' |
| poly l | 5'TATATATATATTTTTGGGG3' |
| poly m | 5'TATATATATTTTTTTTGGG3' |
| poly n | 5'TATATATATTTTTTTTTGG3' |
| poly o | 5'TATATATATTTTTTTTTTG3' |
| poly p | 5'TATATATATATTTTCCCCC3' |
| poly q | 5'TATATATATATTTTTCCCC3' |
| poly r | 5'TATATATATTTTTTTTCCC3' |
| poly s | 5'TATATATATTTTTTTTTCC3' |
| poly t | 5'TATATATATTTTTTTTTTC3' |
| poly u | 5'TATATATATTTTTTTTTTT3' |

| Name | Invention probe |
|---|---|
| probe k | 3'ATATATATATAAAAACCCCC5'-BODIPY FL/C6 |
| probe l | 3'ATATATATATAAAAAACCCC5'-BODIPY FL/C6 |
| probe m | 3'ATATATATATAAAAAAACCC5'-BODIPY FL/C6 |
| probe n | 3'ATATATATATAAAAAAAACC5'-BODIPY FL/C6 |
| probe o | 3'ATATATATATAAAAAAAAAC5'-BODIPY FL/C6 |
| probe p | 3'ATATATATATAAAAAGGGGG5'-BODIPY FL/C6 |
| probe q | 3'ATATATATATAAAAAAGGGG5'-BODIPY FL/C6 |
| probe r | 3'ATATATATATAAAAAAAGGG5'-BODIPY FL/C6 |
| probe s | 3'ATATATATATAAAAAAAAGG5'-BODIPY FL/C6 |
| probe t | 3'ATATATATATAAAAAAAAAG5'-BODIPY FL/C6 |
| probe u | 3'ATATATATATAAAAAAAAAA5'-BODIPY FL/C6 |

TABLE 2

| Nucleic acid probe | Target nucleic acid | Decrease in Fluorescence intensity (%) |
|---|---|---|
| k | k | 93 |
| l | l | 92 |
| m | m | 94 |
| n | n | 92 |
| o | o | 87 |
| p | p | 61 |
| q | q | 66 |
| r | r | 69 |
| s | s | 75 |
| t | t | 73 |
| u | u | 2 |

As is appreciated from Table 2, neither the number of G(s) in a target nucleic acid nor the number of G(s) in an invention probe substantially affects a decrease in fluorescence intensity.

EXAMPLE 7

Target nucleic acids and invention nucleic acid probes of the below-described base sequences were prepared. In a similar manner as in the preceding Example, an investigation was made about effects of the kind of bases in each target nucleic acid and the kind of bases in its corresponding invention nucleic acid probe.

| Name | Target deoxyribooligonucleotide |
|---|---|
| poly w | 5'CCCCCCTTTTTTTTTTTT3' |
| poly X | 5'GGGGGGAAAAAAAAAAAA3' |
| poly Y | 5'TTTTTTCCCCCCCCCCCC3' |
| poly Z | 5'AAAAAAGGGGGGGGGGGG3' |

| Name | Invention probe |
|---|---|
| probe w | BODIPY FL/C6-5'AAAAAAAAAGGGGGG3' |
| probe x | BODIPY FL/C6-5'TTTTTTTTTCCCCCC3' |
| probe y | BODIPY FL/C6-5'GGGGGGGGGAAAAAA3' |
| probe z | BODIPY FL/C6-5'CCCCCCCCCTTTTTT3' |

TABLE 3

| Nucleic acid probe | Target nucleic acid | Fluorescence intensity from probe alone (A) | Fluorescence intensity after addition of target nucleic acid (B) | Decrease in fluorescence intensity, % (C)* |
|---|---|---|---|---|
| W | w | 330 | 380 | −15 |
| X | x | 440 | 430 | 2 |
| Y | y | 40 | 50 | 25 |
| Z | z | 360 | 30 | 92 |

*Decrease in fluorescence intensity, % (C) = {(A-B)/A} × 100

As is appreciated from Table 3 and the preceding Example, a substantial decrease takes place in fluorescence intensity (i) when an end of an invention probe labeled with a fluorescent dye is composed of C and hybridization of a target nucleic acid forms a G-C pair, or (ii) when an end of an invention probe labeled with a fluorescent dye is composed of a base other than C and at least one G exists on a side closer to the 3' end of a target nucleic acid than a base pair formed of a base at a location where the invention probe is labeled with the fluorescent dye and a base of the target nucleic acid.

EXAMPLE 8

Concerning the kinds of dyes usable for labeling nucleic acid probes of the present invention, an investigation was made in a similar manner as in the preceding Examples. As an invention probe, the probe z of Example 7 was used. As a target nucleic acid, on the other hand, the oligonucleotide z of Example 7 was employed.

The results are shown in Table 4. As is readily envisaged from this table, illustrative fluorescent dyes suitable for use in the present invention can include FITC, "BODIPY FL", "BODIPY FL/C3", 6-joe, and TMR.

TABLE 4

| Fluorescent dye | Decrease in fluorescence intensity (%) |
|---|---|
| FITC | 90 |
| "BODIPY FL" | 95 |
| "BODIPY FL/C3" | 96 |
| "BODIPY FL/C3" | 97 |
| 6-joe | 75 |
| TMR | 93 |

Incidentally, the decreases (%) in fluorescence intensity were calculated in a similar manner as in Example 7.

EXAMPLE 9
Preparation of Nucleic Acid Probe

An oligonucleotide was purchased from Midland Certified Reagent company, U.S.A. as in Example 1. The oligonucleotide had a base sequence of (5') CATCCCCACCTTCCTCCCAGTTGACCCCGGCAGTC (3') (35 base pairs) hybridizable specifically to the 16S rNA base sequence of KYM-7 strain, said base sequence being equivalent to the base sequence ranging from the $1156^{th}$ base to the $1190^{th}$ base of the 16S rRNA of *Escherichia coli* JM109, contained deoxyribonucleotides at the $1^{st}$ to $16^{th}$ bases and the $25^{th}$ to $35^{th}$ bases, respectively, said methyl-modified ribonucleotides being modified with methyl groups at the OH group at the 2' position on the carbon atom or ribose, and was modified with $-(CH_2)_7-NH_2-$ at the phosphate group of the 5'-terminal group of the 35 base pairs. From Molecular Probes, Inc., "FluoroReporter Kit F-6082" (trade name) was also purchased, which contained not only "BODIPY FL/C6" propionic acid succinimidyl ester but also a reagent for conjugating the compound to the amine derivative of the oligonucleotide. The kit was caused to act on the above oligonucleotide, whereby a nucleic acid probe labeled with "BODIPY FL/C6" was synthesized. The synthesized product so obtained was purified as in Example 1, whereby the nucleic acid probe labeled with "BODIPY FL/C6" was obtained with a yield of 23% as calculated relative to 2 mM of the starting oligonucleotide. This probe was named "35-nucleotides-chained 2-O—Me probe".

Using a DNA synthesizer, a riboxyoligonucleotide having a base sequence of (5')AGGCCGGCCCTTGACTTTCCT (3') was synthesized as in the above to provide it as a forward-type hepter probe. On the other hand, a riboxyoligonucleotide having a base sequence of (5') AUGGGAGUuCAGUAGUACCCGCAAUGCUGGUCC (3') was synthesized by using a DNA synthesizer, thereby providing it as a reverse-type helper probe.

Figure 2:
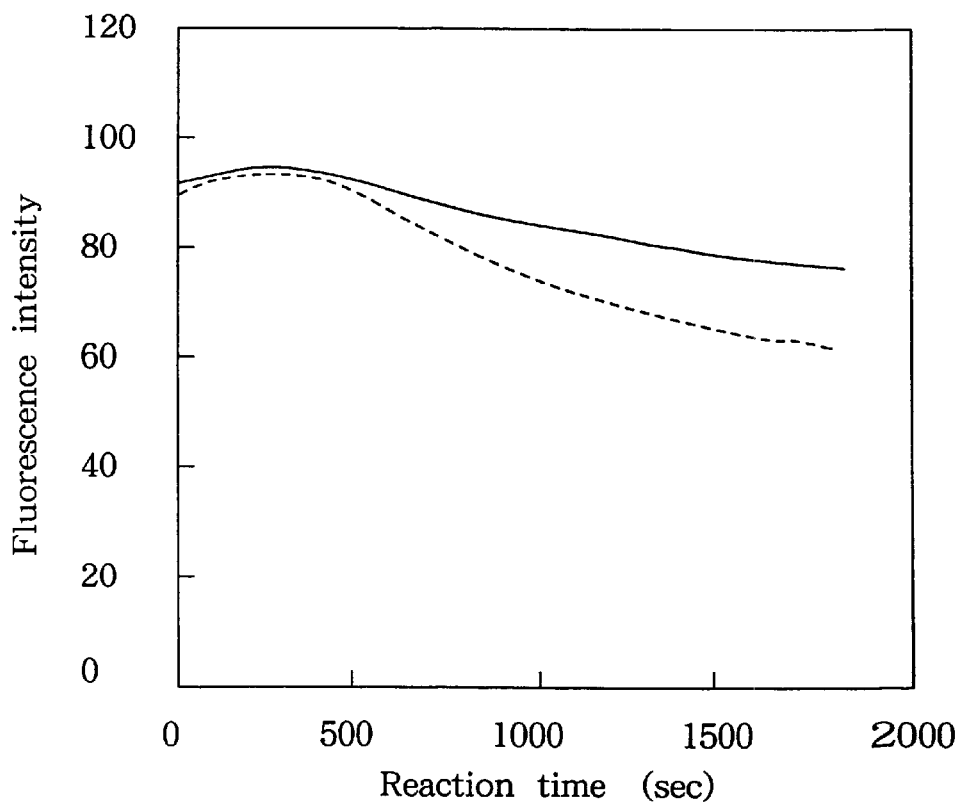

The above-described 16S rRNA was subjected to heat treatment at 95° C. for 5 minutes, and was then added to a probe solution which had been maintained under the below-described reaction conditions. By a fluorescence measuring instrument "Perkin-Elmer LS-50B" (trade name), the intensity of fluorescence was measured. The results are shown in FIG. 2. Incidentally, data obtained by using 16S rRNA which was not subjected to the above-described heat treatment are plotted as a control. It is understood from FIG. 2 that substantial decreases in fluorescence intensity took place in the experimental group in the experimental group subjected to heat treament. These results indicate that heat treatment of 16S rRNA at 95° C. induces stronger hybridization with the probe according to the present invention.

Reaction Conditions 16S rRNA: 10.0 nm

Probe: 25 nM

Buffer: 100 mM succinic acid, 125 mM lithium hydroxide, 8.56% lithium dodecylsulfite, pH 5.1

Temperature: 70° C.

EXAMPLE 10

Effects of helper probe on the efficiency of hybridization

Invention probes and helper probes, which were to be hybridized to the above-described 16S rRNA, were prepared in a similar manner as described above. Under conditions to be described subsequently herein, an investigation was made about effects of a 2'-O—Me probe of the present invention, effects of the length of a nucleotides chain in the probe and effects of a helper probe. The results are presented in diagrams A, B, C and D in FIG. 3. It is appreciated from these diagrams that the 2'-O—Me probe according to the present invention contributes to the efficiency of hybridization. It is also understood that the helper probe is effective in increasing the efficiency of hybridization when the base strand of the 2'-O—Me probe is short.

1) The same 35-nucleotides-chained 2'-O—Me probe as described above.
2) A probe having the same base sequence as the 35-nucleotides-chained 2'-O—Me described above under 1) except that the oligonucleotide is formed of a deoxyribonucleotide (33-nucleotides-chained DNA probe).
3) A probe having the same base sequence as the 35-nucleotides chained 2'-O—Me described above under 1) except that the nucleotides ranging over 8 bases from the 5' end and 16 bases from the 3' end were removed (17-nucleotides-chained 2-O—Me probe).
4) A probe having the same base sequence as the 33-nucleotides-chained 2-O—Me probe described above under 2) except that a nucleotide ranging over 16 bases from the 3' end was removed (17-nucleotides-chained DNA probe).
5) A helper probe obtained by modifying the OH groups of the central 8 bases of the above-described forward-type helper probe with methyl groups (forward-type 2-O—Me-helper probe).
6) A helper probe obtained by modifying the OH groups of the central 8 bases of the above-described reverse-type helper probe with methyl groups (reverse-type 2-O—Me-helper probe).
7) A helper probe having the same base sequence as the above-described forward helper probe except that the oligonucleotide is formed of a deoxyribonucleotide (forward-type DNA helper probe).
8) A helper probe having the same base sequence as the above-described reverse helper probe except that the oligonucleotide is formed of a deoxyribonucleotide (reverse-type DNA helper probe).
9) A ribooligonucleotide having a base sequence of 5')GUGACGGUCACUAUUUGACCUCCUUCCACCCC(3') (35-base ribooligonucleotide).
10) A ribooligonucleotide having a base sequence of 5')GUGACGGUCACUAUUUG (3') (17-base ribooligonucleotide).

Reaction Conditions

Concentration of 16S rPNA: 10 nM

Concentration of probe: 25 nM

Helper probe concentration: 1 $\mu$M

Buffer composition: 100 mM succinic acid, 125 mM lithium hydroxide, 8.5% lithium dodecylsulfite, pH 5.1

Reaction Temperature

70° C. (for 35-nucleotide-chained 2-O—Me probe)

65° C. (for 17-nucleotides-chained 2-O—Me probe and 33-nucleotides-chained DNA probe)

50° C. (for 17-nucleotides-chained DNA probe)

EXAMPLE 12

Preparation of working curve for rRNA determination

At diverse concentrations within a range of from 0.1 to 10 M, the above-described rRNA was heated at 95° C. for 5 minutes. The resulting nucleic acid solutions were added to aliquots of a reaction mixture, respectively. The reaction mixture had been prepared and maintained under the below-described reaction conditions. Upon elapsed time of 1,000 seconds, decreases in fluorescence intensity were measured using "Perkin-Elmer LS-50B". The results are plotted in FIG. 4. It is appreciated from the diagram that the working curve shows linearity in the range of from 0.1 to 10 nM.
Reaction Conditions
    Concentrations of 33-nucleotides-chained 2-O—Me probe: 10 nM
    Buffer composition: 100 mM succinic acid, 125 mM lithium hydroxide, 8.5% lithium dodecylsulfite, pH 5.1
    Reaction temperature: 70° C.

EXAMPLE 12

Florescent in situ hybridization assay

In a similar manner as described above, 35-nucleotides-chained 2-O—Me probe and 36-nucleotides-chained 2-O—Me probe according to the present invention were prepared for hybridization to the respective rRNAs of Cellulomonas sp. KYM-7 (FERM P-16806) and Agrobacterium sp. KYM-8 (FERM P-11358), respectively. Those probes had the following base sequences:

35-nucleotides-chained 2-O—Me probe for assaying the rRNA of Cellulomonas sp. KYM-7:

(5') CATCCCCACCTTCCTCCCCCGGCAGTC (3')

(the boxed bases are modified with methyl groups)
    36-nucleotides-chained 2-O—Me probe for assaying the rRNA of Agrobacterium sp. KYM-8:

(5') CATCCCCACCTTCCTC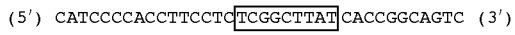CACCGGCAGTC (3')

(the boxed bases are modified with methyl groups)

Cellulomonas sp. KYM-7 (FERE P-16806) and Agrobacterium sp. KYM-8 (FERM P-11358) were co-cultured with the below-described medium composition under the below-described cultivation conditions. Co-cultures were sampled at various phases of the co-cultivation. From each of the co-cultures, rRNAs were prepared using "RNeasy Maxikit" (trade name; product of QIAGEN GmbH (Hilden, Germany). Those rRNAs were heated at 95° C. for 5 minutes, and then added to the reaction mixture which had been maintained under the reaction conditions. After they were reacted at 70° C. for 1,000 seconds, a decrease in fluorescence intensity was measured using "Perkin-Elmer LS-50B". The results are plotted in FIG. 5. Incidentally, the total rRNA was measured using "RiboGreen RNA Kit" (trade name; product of Molecular Probe, Inc. (Eugene, Oreg., U.S.A.).

As is appreciated from the diagram, the mobilizations of the rRNks of the respective cell strains were consistent with that of the total rRNA. This indicates that the method of the present invention can be effectively used in fluorescent in situ hybridization assays,
Composition of Culture Medium (g/L)
    Starch, 10.0; aspartic acid, 0.1; $K_2HPO_4$, 5.0; $KH_2PO_4$, 5.0; $KH_2PO_4$, 2.0; $MgSo_4.7H_2O$, 0.2; NaCl, 0.1; $(NH_4)_2SO_4$, 0.1.
Cultivation Conditions
    The above-describe cell strains were cultivated beforehand on a slant medium. One roopful of the culture was collected from the slant medium, and was then inoculated to the above-described sterilized nutrient broth (NB) in an Erlenmeyer flask. The strains were cultured at 30° C. and 150 rpm under shaking.
Reaction Conditions
    Concentrations of 33-nucleotides-chained 2-O—Me probe: 1.0 to 10 nM
    Buffer composition: 100 mM succinic acid, 125 mM lithium hydroxide, 8.5% lithium dodecylsulfite, pH 5.1
    Reaction temperature: 70° C.

A method for analyzing polymorphism and mutation of a target nucleic acid or gene will hereinafter be described in Example 13.

EXAMPLE 13

Four oligonucleotides with the below-described base sequences were synthesized using the same DNA synthesizer as that employed in Example 5. Further, an invention nucleic acid probe having the below-described base sequence was also synthesized in a similar manner as in Example 5. The oligonucleotides were separately hybridized with the probe in solutions. An investigation was then made as to whether or not a single base substitution can be determined from a change in fluorescence intensity. The base sequence of the nucleic acid probe according to the present invention is designed such that, if G exists at the 3' end of any one of the target oligonucleotides, it matches 100% with the base sequence of the particular oligonucleotide. The hybridization temperature was set at 40° C. at which all base pairs between the probe and the target oligonucleotide can hybridize 100%. The concentrations of the probe and target oligonucleotides, the concentration of a buffer solution, a fluorimeter, fluorescence measuring conditions, experimental procedures, and the like were set or chosen as in Example 5.

Invention probe:
        3'TTTTTTTTGGGGGGGGC5'BODIPY FL/C6
    Target nucleotide No. 1: 5'AAAAAAAACCCCCCCCA3'
    Target nucleotide No. 2: 5'AAAAAAAACCCCCCCC3'
    Target nucleotide No. 3: 5'AAAAAAAACCCCCCCCI3' (I: hypoxanthine)
    Target nucleotide No. 4: 5'AAAAAuAAACCCCCCCG3'

The results are shown in Table 5. As is appreciated from the table, no change in fluorescence intensity was observed in the case of the target oligonucleotides Nos. 1 to 3, but in the case of the target oligonucleotide No. 4, a decrease as much as 84% was observed.

TABLE 5

| Target oligo-nucleotide | Initial fluorescence intensity (A) | Fluorescence intensity after hybridization (B) | (A-B)/B |
|---|---|---|---|
| No. 1 | 340 | 350 | −0.03 |
| No. 2 | 332 | 328 | 0.01 |
| No. 3 | 343 | 336 | 0.02 |
| No. 4 | 345 | 52 | 0.84 |

In the method of the present invention for analyzing data (for example, the data in columns A and B in Table 5) obtained by the method for analyzing or determining polymorphism and/or mutation of a target nucleic acid or gene (for example, the target oligonucleotide No. 1, 2, 3 or 4), the processing to correct a fluorescence intensity of a reaction system, said fluorescence intensity being obtained when a target nucleic acid or gene is hybridized with a nucleic acid probe labeled with a fluorescent dye (for example, the above-described nucleic acid probe), by a fluorescence intensity of the same reaction system when the target nucleic acid or gene is not hybridized with the nucleic acid probe means the calculation of (A–B)/B in Table 3.

From the above results, it has been found that, when a target nucleic acid is a double-stranded nucleic acid, substitutions of G→A, G←A, C→T, C←T, G→C and G←C can be detected.

EXAMPLE 14

A model of A DNA chip according to the present invention is illustrated in FIG. 6. Firstly, a modified probe and a surface-treated slide glass are provided first. The modified probe had been prepared by introducing an amino group onto the 3'-OH group at the 3' end of the invention probe, 3'TTTTTTTTGGGGGGGGC5'BODIPY FL/C6, prepared in Example 13. On the other hand, the surface-treated slide glass had been prepared by treating a slide glass with a silane coupling agent which contained epoxy groups as reactive groups. A solution with the modified probe contained therein was applied in spots onto the surface-treated slide glass by a DNA chip production apparatus, "GMS™ 417 ARRAYER" (manufactured by TAKARA SHUZO CO., LTD., Kyoto, Japan). As a result, the modified probe is bound at the 3' end onto a surface of the slide glass. The slide glass is then placed for 4 hours or so in a closed vessel to bring the reaction to completion. The slide glass was alternately dipped in 0.1% SDS solution and water, twice in each of the solution and water, for about 1 minute each time. Further, the slide glass was immersed for about 5 minutes in a boron solution, which had been prepared by dissolving $NaBH_4$ (1.0 g) in water (300 mL). Shortly after the slide glass was placed for 2 minutes in water of 95° C., the slide glass was alternately dipped in 0.1% SDS solution and water, twice in each of the solution and water, for about 1 minute each time, so that reagents were washed off. The slide glass was then dried. As a result, a DNA chip according to the present invention was prepared.

Further, arrangement of a minute temperature sensor and a microheater on the lower side of the slide glass at a position corresponding to each spot of the modified probe makes it possible to provide the DNA chip of the present invention with high performance.

A description will next be made of a determination of a target nucleic acid or gene by the DNA chip. No change takes place in fluorescence intensity where the target nucleic acid or gene is not hybridized with the probe, where no G-C pair is formed at the fluorescent-dye-labeled end even if they are hybridized together, or where at least one G (guanine) base does not exist in the base sequence of the target nucleic acid or gene at a position 1 to 3 bases apart from an end base portion where the probe and the target nucleic acid or gene are hybridized with each other. However, the intensity of fluorescence decreases when hybridization takes place. This fluorescence intensity can be measured by using a DNA chip analyzer, "GMS™ 418 Array Scanner" (manufactured by TAKARA SHUZO CO., LTD.).

Methods of the present invention for PCR assay will hereinafter be described in Examples 15–19.

EXAMPLE 15

Using as a target nucleic acid the 16S rRNA gene in the genome DNA of *Escherichia coli*, a primer labeled with "BODIPY FL/C6" was prepared for the amplification of the nucleic acid.

Preparation of Primer 1 (Eu800R: Reverse Type)

A deoxyribooligonucleotide having a base sequence of (5')CATCGTTTACGGCGTGGAC(3') was synthesized using a DNA synthesizer, "ABI394" (trade name; manufactured by Perkin-Elmer, Corp.). An oligonucleotide, which had been prepared by treating the phosphate group at the 5' end of the oligodeoxyribonucleotide with phosphatase to form cytosine and then bonding $-(CH_2)_9-NH_2$ to the OH group on the carbon atom at the 5'-position of the cytosine, was purchased from Midland Certified Reagent Company. From Molecular Probes, Inc., "FluoroReporter Kit F-6082" (trade name) was also purchased, which contained not only "BODIPY FLY" propionic acid succinimidyl ester but also a reagent for conjugating the compound to the amine derivative of the oligonucleotide. The kit was caused to act on the above-purchased oligonucleotide, whereby Primer 1 of the present invention labeled with "BODIPY FL/C6" was synthesized.

Purification of Synthesized Product

The synthesized product was dried into a dry product. The dry product was dissolved in 0.5 M $Na_2CO_3/NaHCO_3$ buffer (pH 9.0). The solution was subjected to gel filtration through "NAP-25 Column" (trade name, product of Pharmacia AB, Uppsala, Sweden), whereby unreacted substances were removed. Further, reversed phase HPLC (B gradient: 15 to 65%, 25 minutes) was conducted under the below-described conditions. An eluted main fraction was collected. The collected fraction was lyophilized, whereby Primer 1 of the present invention was obtained with a yield of 50% as calculated relative to 2 mM of the starting oligonucleotide, The above-described reversed phase chromatography was conducted under the following conditions:

Eluting solvent A: 0.05 N TEAA 5% $CH_3CN$

Eluting solvent B (for gradient elution): 0.05 N TEAA 40% $CH_3CN$

Columns: CAPCEL PAK C18 (trade name), 6×250 mm

Elution rate: 1.0 mL/min

Temperature: 40° C.

Detection: 254 nm

EXAMPLE 16

Preparation of Primer 2 (Eu500R/forward: Forward Type)

Primer 2 composed of a deoxyribooligonucleotide, which had a base sequence of (5')CCAGCAGCCGCGGTAATAC (3'), and a fluorescent dye ("BODIPY FL/C6") labeled to the 5' end of the deoxyribooligonucleotide, was prepared with a yield of 50% in a similar manner as in Example 13.

EXAMPLE 17

Using a test tube containing a liquid culture medium (5 mL; composition: NB, 0.08 g/100 mL) of sterilized neutrient broth (NB)(product of Difco), *Escherichia coli* JM109 was cultivated overnight at 37° C. under shaking. A 1.5-mL aliquot of the culture was centrifuged in a 1.5-mL centrifuge tube, whereby cells were obtained. From the cells, genome DNA was extracted using "DNeasy Tissue Kit" (trade name, product of QIAGENE GmbH, Hilden, Germany). The extraction was conducted following the protocol of the kit. As a result, a 17-ng/μL DNA solution was obtained.

EXAMPLE 18

Using the genome DNA of the above *E. coli* strain, Primer 1 and/or Primer 2, PCR reactions were conducted by a method known per se in the art while using "LightCycler™ System" (trade name) marketed from Roche Diagnostics, Mannheim, Germany. Operations were conducted following the manual of the system.

In the above system, PCR was conducted as specified in the manual except that Primer 1 and/or Primer 2 of the present invention were used in place of nucleic acid probes (two nucleic acid probes making use of the FRET phenomenon) and a general primer (a general primer not labed with any fluorescent dye), both of which are listed in the manual).

PCR was conducted in a hybridization mixture of the following components:

| | |
|---|---|
| *E. coli* genome DNA solution<br>(final concentration: 0 to 6 ng/20 μL)<br>(final copy number: 0 to 2.4 × 10$^6$ copies) | 3.5 μL |
| Primer solution<br>(final concentration: 0.08 μM) | 0.8 μL |
| Taq solution | 10.0 μL |
| "MiliQ" purified water | 5.7 μL |
| Final whole volume | 20.0 μL |

Incidentally, the experiments were conducted by using the target nucleic acid, *E. coli* 16S rDNA, at the concetrations of the respective experimental groups shown in the brief description of FIG. 7 and also by using the primers in the combinations of Primer 1 and/or Primer 2 also shown in the brief description of FIG. 7.

The above Taq solution is a mixed solution of the

| | |
|---|---|
| Taq solution | 96.0 μL |
| "MiliQ" purified water | 68.2 μL |
| Taq DNA polymerase solution | 24.0 μL |
| Taq start | 3.8 μL |

Incidentally, these Taq solution and Taq DNA polymerase solution were both included in the "DNA Master Hybridization Probe Kit" (trade name; product of Roche Diagnostics, Mannheim, Germany). Specifically, as the Taq DNA. polymerase solution, the 10×conc. solution (redcap) was used by diluting it tenfold. Further, Taq start is an antibody for the Taq DNA polymerase and is marketed by Clontech Laboratories, Inc., Palo Alto, Calif., U.S.A. Addition of Taq start to a reaction mixture can suppress activity of Taq DNA polymerase up to 70° C.

The following reaction conditions were used.

| | |
|---|---|
| Denaturation | Initial: 95° C., 120 seconds<br>Second and onwards: 95° C., 120 seconds |
| Annealing | 57° C., 5 seconds |

Measurements were conducted using "LightCycler™ System" (manufactured by Roche Diagnostics, Mannheim Germany). For each measurement, the detector F1 was used out of the detectors F1–F3 included in the system, and the gain and excitation level of the detector were set at 10 and 75, respectively.

The results are shown in FIG. 7 and FIG. 8. It is appreciated from FIG. 7 and FIG. 8 that the number of cycles at the time of observation of a decrease in fluorescence emission from the fluorescent dye and the number of copies of *E. coli* 16S rDNA as the target nucleic acid are proportional to each other. In these diagrams, decreases in fluorescence emission from the fluorescent dye are expressed in terms of decreases in the intensity of fluorescence.

FIG. 9 shows a working line for *E. coli* 16S rDNA, in which the number of copies of *E. coli* 16S rDNA is expressed as a function of cycles. The correlation coefficient was 0.9973, so that extremely good correlation was exhibited.

As is understood from the above results, use of the quantitative PCR method of the present invention makes it possible to count the number of copies of a target nucleic acid at the beginning. This means that the concentration of the target nucleic acid can be determined.

EXAMPLE 19

In Example 18, PCR was conducted using the invention probes as primers. In this example, however, PCR according to the present invention was conducted under the following conditions by using a primer of the present invention as opposed to two probes required in the conventional method making use of the FRET phenomenon.

a) Target nucleic acid: 16S rDNA of *Escherichia coli*
b) Primers:
    Forward primer E8F: (3') AGAGTTTGATCCTGGCTCAG(5')
    Reverse primer E1492R: GGTTACCTTGTTACGACTT(5')
c) Probe: BODIPY FL-(3')CCTTCCCACATCGTTT(5')
d) PCR apparatus: "LightCycler™ System" (manufactured by Roche Diagnostics, Mannheim Germany)
e) Conditions for PCR:
    Denaturation: 95° C. for 0 second (95° C. for 60 seconds in the first cycle only)
    Annealing:. 50° C. for 5 seconds
    Extension: 72° C. for 70 seconds
    Total cycle number: 70 cycles
f) Fluorescence assay (measurement):
    Assay (measurement) was performed once after each of denaturation and annealing in each cycle.
g) Composition of reaction mixture:
    Total volume: 20 μL
    Amount of DNA polymerase ("TaKaRa Ex taq"): 0.5 U
    Amount of TaqStart antibody: 0.3 μL
    Concentration of primer: 0.2 μM (common to both primers)
    Concentration of probe: 0.05 μM
    Concentration of $MgCl_2$: 2 mM
    Conc. of BSA (bovine serum albumin): 0.25 mg/mL
    Concentration of dNTPs: 0.2 mM (for each nucleotide)

The results are shown in FIG. 10. It is understood from the diagram that the number of cycles at the time of observation of a decrease in fluorescence emission from the fluorescent dye and the number of copies of *E. coli* 16S rDNA as the target nucleic acid are proportional to each other.

As is understood from the above results, use of the quantitative PCR method of the present invention makes it possible to count the number of copies of a target nucleic acid at the beginning. This means that the concentration of the target nucleic acid can be determined.

In the subsequent Examples, the data analysis method of the present invention for analyzing, data obtained by using the above-described quantitative PCR method of the present invention will be described.

EXAMPLE 20

Using, as a target nucleic acid, human genome DNA (human β-globin) (TaKara Catalog Product No. 9060) (product of TAKARA SHUZO CO., LTD., Kyoto Japan) (hereinafer called "the human genome DNA"), a primer labeled with "BODIPY FL/C6" was prepared for the amplification of the nucleic acid.

Preparation of Primer KM38+C (reverse type)

A deoxyribooligonucleotide having a base sequence of (5')CTGGTCTCCTTAAACCTGTCTTG(3') was synthesized using a DNA synthesizer, "ABI394" (trade name; manufactured by Perkin-Elmer, Corp.). An oligonucleotide, which had been prepared by treating the phosphate group at the 5' end of the oligodeoxyribonucleotide with phosphatase to form cytosine and then bonding —$(CH_2)_9$—$NH_2$ to the OH group on the carbon atom at the 5'-position of the cytosine, was purchased from Midland Certified Reagent Company. From Molecular Probes, Inc., "FluoroReporter Kit F-6082" (trade name) was also purchased, which contained not only "BODIPY FL" propionic acid succinimidyl ester but also a reagent for conjugating the compound to the amine derivative of the oligonucleotide. The kit was caused to act on the above-purchased oligonucleotide, whereby Primer KM38+C of the present invention labeled with "BODIPY FL/C6" was synthesized.

Purification of Synthesized Product

The synthesized product was dried into a dry product. The dry product was dissolved in 0.5 M $Na_2CO_3$/$NaHCO_3$ buffer (pH 9.0). The solution was subjected to gel filtration through "NAP-25 Column" (trade name, product of Pharmacia AB, Uppsala, Sweden), whereby unreacted substances were removed. Further, reversed phase HPLC (B gradient: 15 to 65%, 25 minutes) was conducted under the below-described conditions. An eluted main fraction was collected. The collected fraction was lyophilized, whereby Primer KM38+C of the present invention was obtained with a yield of 50% as calculated relative to 2 mM of the starting oligonucleotide.

The above-described reversed phase chromatography was conducted under the following conditions:

Eluting solvent A: 0.05 N TEAA 5% $CH_3CN$

Eluting solvent B (for gradient elution): 0.05 N TEAA 40% $CH_3CN$

Column: CAPCEL PAK C18 (trade name), 6×250 mm

Elution rate: 1.0 mL/min

Temperature: 40° C.

Detection: 254 nm

EXAMPLE 21

Preparation of Primer KM29 (Forward Type)

A deoxyribooligonucleotide having a base sequence of (5')GGTTGGCCAATCTACTCCCAGG(3') was synthesized in a similar manner as in Example 18.

Comparative Example 1

This Comparative Example is directed to use of a data analysis software which did not include the processing step of the present invention that an intensity of fluorescent during an extending reaction of a nucleic acid is divided using an intensity of fluorescent at the time of a thermal denaturing reaction [i.e., the processing of the formula (1)].

Using the above-described human genome DNA, Primer KM38+C and Primer KM29, PCR reactions were conducted by "LightCycler™ System" (manufactured by Roche Diagnostics, Mannheim Germany). The intensity of fluorescence was measured in each cycle.

Incidentally, the PCR in this Comparative Example employed the above-described primers labeled with the fluorescent dye, and is a novel real-time quantitative PCR method in which a decrease in fluorescence emission is measured rather than an increase in fluorescence emission. Analysis of data was conducted using the software of the system itself. The PCR in this Comparative Example was conducted following the manual of the system except that the invention primers KM38+C and KM29 were used instead of the nucleic acid probes listed in the (two probes making use of the FRET phenomenon) or an ordinary primer (an ordinary primer not labeled with any fluorescent dye).

PCR was conducted in a hybridization mixture of the following components:

| | |
|---|---|
| Human genome DNA | 1.0 µL |
| (final concentration: 1 to 10,000 copies) | |
| Primer solution | 4.0 µL |
| (final concentration: 0.1 µM) | |
| Taq solution | 10.0 µL |
| "MiliQ" purified water | 5.0 µL |
| Final whole volume | 20.0 µL |

Incidentally, the experiments were conducted by using the human genome at the concetrations of the respective experimental groups shown in the brief description of FIG. 11.

The following reaction conditions were used.

| | |
|---|---|
| Denaturation | Initial: 95° C., 60 seconds |
| Second and onwards: | 95° C., 10 seconds |
| Annealing | 60° C., 5 seconds |
| DNA extending reaction: | 72° C., 17 seconds |

Measurements were conducted using "LightCycler™ System" (manufactured by Roche Diagnostics, Mannheim Germany). For each measurement, the detector F1 was used out of the detectors F1–F3 included in the system, and the gain and excitation level of the detector were set at 10 and 75, respectively.

PCR was conducted as described above, during which the intensities of fluorescence in individual cycles were measured. The results are shown in FIG. 11. Described specifically, with respect to each of the human genome DNAs of the respective copy numbers, the intensity of fluorescence was measured at the time of a denaturing reaction and also at the time of a nucleic acid extending reaction, both in each cycle, and was printed. It is observed that the intensity of fluorescence remained constant at the time of the denaturing reaction irrespective of the cycle but a decrease in fluorescence took place from the 25th cycle at the time of the nucleic acid extending reaction. It is also understood that this decrease occurs earlier as the number of copies of the human genome DNA increases.

As is shown in FIG. 11, the intensities of fluorescence in initial cycles were not constant irrespective of the number of copies of the human genome DNA. The following steps (b)–(i) were, therefore, added to the data analysis method for use in this Comparative Example.

(b) Assuming that the intensity of fluorescence in the $10^{th}$ cycle is 1, the intensity of fluorescence in each cycle is converted, namely, calculation is conducted in accordance with the following formula (8):

$$C_n = (72)/F_{10}(72) \tag{8}$$

where $C_n$: converted value of the intensity of fluorescence in each cycle, $F_n(72)$: the intensity of fluorescence after extending reaction at 72° C. in each cycle, and $F_{10}(72)$: the intensity of fluorescence in the $10^{th}$ cycle.

(c) Each converted value obtained in step (b) is displayed on a display and/or printed as a function of cycle.

(d) From the converted value in each cycle as obtained in step (b), the rate of a change in fluorescence intensity (decrease or quench, %) is calculated in accordance with the following formula (9):

$$F_{dn}=\log\{100 - C_n \times 100)\} \tag{9}$$

$$F_{dn}=2 \log\{1-C_n\} \tag{9}$$

where $F_{dn}$: the rate of a change in fluorescence intensity (decrease or quench, %), and $C_n$: the value obtained in accordance with the formula (8).

(e) Each converted value obtained in step (d) is displayed on a display and/or printed as a function of cycle.

(f) Data processed in step (d) are compared with 0.5 as a threshold, and the number of cycles the data of which reach the threshold is counted.

(g) A graph is prepared by plotting values, which have been counted in step (f), along X-axis and the numbers of copies before the initiation of the reaction along Y-axis.

(h) The graph prepared in step (g) is displayed on a display or printed.

(i) A correlation coefficient or relational formula of the line drawn in step (h) is calculated.

(j) The correlation coefficient or relational formula calculated in step (i) is displayed on a display or printed.

Using the above-described data analysis software, the data obtained in FIG. 11 were then processed as will be described hereinafter.

FIG. 12 is a print-out of the data processed in step (b) [process (c)]. Namely, assuming that the intensity of fluorescence in the $10^{th}$ cycle was 1, the fluorescence intensities in the individual cycles were converted, and the converted values were plotted against the corresponding cycles.

FIG. 13 is a print-out of the data processed in step (d) [process (e)]. Namely, decreases (%) (quenches, %) of the respective fluorescence intensities were calculated from the plotted values in FIG. 12, and the values so calculated were plotted against the corresponding cycles.

FIG. 14 is a print-out of the graph prepared in step (g) based on the data processed in step (f) [step (h)]. Namely, it is a graph obtained by using a decrease of 0.5 in fluorescence intensity as a threshold, plotting along X-axis the number of cycles in which the threshold was reached, and also plotting along Y-axis the numbers of copies of the human genome DNA before the initiation of the respective reactions. The correlation coefficient (R2) of the line in this graph was calculated in step (i), and was then printed [step (j)]. The correlation coefficient was 0.9514. As is understood, it was hardly possible, with this correlation coefficient, to determine an accurate number of copies this correlation coefficient was

EXAMPLE 22

This Example is directed to an experiment in which processing of data was performed by using the data analysis method of the present invention.

PCR was conducted in a similar manner as in Comparative Example 1.

The processing of the data was performed through similar steps as in Comparative Example 1 except that the following step (a) was added before the step (b) and the steps (b), (d) were modified as will be described below.

(a) The intensity of fluorescence in each cycle in a reaction system in which an amplified nucleic acid hybridized to a nucleic acid primer labeled with a fluorescent dye [namely, the intensity of fluorescence at the time of a nucleic acid extending reaction (72° C.)] was corrected in a correction processing step such that the intensity of fluorescence was divided by the intensity of fluorescence in the reaction system measured at the time of dissociation of the hybrid complex of the amplified nucleic acid and the nucleic acid primer [namely, the intensity of fluorescence at the time of the nucleic acid denaturing reaction (95° C.)], that is, the actually-measured intensities of fluorescence were corrected in accordance with the following formula (1):

$$f_n = f_{hyb,n}/f_{den,n} \tag{1}$$

where $f_n$: correction value for the intensity of fluorescence in each cycle, $f_{hyb,n}$: the intensity of fluorescence at 72° C. in each cycle, and $f_{den,n}$: the intensity of fluorescence at 95° C. in each cycle.

It is FIG. 15 that was obtained by plotting the thus-obtained values against the corresponding cycles.

(b) A processing step that the values correction-processed by formula (1) in the respective cycles were introduced into the formula (3) to calculate the rates of changes (decreases or quenches, %) in fluorescence between the samples in the respective cycles, namely, a step for performing processing in accordance with the following formula (10):

$$F_n = f_n/f_{25} \tag{10}$$

where $F_n$: processed value of each cycle, $f_n$: value of each cycle as obtained in accordance with formula (1), and $f_{25}$: value of the $25^{th}$ cycle as obtained in accordance with formula (1).

Formula (10) is similar to formula 3 except for a=25.

(d) A step that the processed value of each cycle as obtained in step (b) was subjected to processing in accordance with formula (6) to obtain the logarithm of the rate of a change (decrease or quench, %) in fluorescence intensity, namely, a step for performing processing in accordance with the following formula (11):

$$\log\{(1-F_n) \times 100\}) \tag{11}$$

where $F_n$: value obtained in accordance with formula (10).

Formula (11) is similar to formula (6) except for b=10 and A=100.

The above results are shown in FIGS. 16 and 17.

FIG. 16 is a print-out obtained by plotting the values, which have been processed in steps (a) and (b), against the corresponding cycles.

FIG. 17 is a print-out obtained by processing the values, which have been obtained in FIG. 16, in a similar manner as in step (d) and then plotting the thus processed values against the corresponding cycles.

Next, based on the graph of FIG. 17, processing was performed through steps (f), (g) and (h). Described specifically, as in Comparative Example 1, 0.1, 0.3, 0.5, 0.7, 0.9 and 1.2 were chosen as thresholds for log (rates of changes in fluorescence intensity, %). The numbers of cycles in which the logarithums reached the thresholds were plotted along X-axis, while the numbers of copies of the human genome DNA before the initiation of reactions were plotted along Y-axis, whereby working lines were drawn. The results are shown in FIG. 18. Correlation coefficients ($R^2$) determined by conducting processing in steps (i) and (j) with respect to those working lines were 0.998, 0.999, 0.9993, 0.9985, 0.9989 and 0.9988, respetively. From those correlation coefficients, it was able to confirm that adoption of 0.5 as a threshold (correlation coefficient: 0.9993) is desired. It is understood that, with a working line having this correlation coefficient, the number of copies before initiation of a reaction can be accurately determined with respet to a nucleic acid sample the number of copies of which is unknown.

EXAMPLE 23

This Example is directed to an analysis of a melting curve of a nucleic acid and also to an analysis of a Tm value.

A software comprising the following steps was created: 1) with respect to a nucleic acid amplified by the novel PCT method of the present invention, gradually heating the amplified nucleic acid from a low temperature until the nucleic acid is completely denatured (for example, from 50° C. to 95° C.), or gradually lowering it; 2) in step 1), measuring the intensity of fluorescence at short time intervals (for example, at intervals equivalent to temperature rises of from 0.2° C. to 0.5° C.) ; 3) displaying the measurement results of step 2) on a display as a function of time, namely, displaying a melting curve of the nucleic acid; 4) differentiating the melting curve obtained in step 3); 5) displaying, on a display, derivatives (−dF/dT, F: fluorescence intensity, T: time) obtained in step 4); and 6) determining a point of inflection from the derivatives obtained in step 5). Using "LightCycler™ System" (manufactured by Roche Diagnostics, Mannheim Germany) in which a computer-readable recording medium with the data analysis software recorded therein had been installed, the novel real-time quantitative PCR reaction of the present invention was conducted to analyze the melting curve of the nucleic acid. In the present invention, the intensity of fluorescence increases with the temperature.

With respect to 1 copy and 10 copies of the same human genome DNA as in Example 22, PCR was conducted in a similar manner as in Example 20. FIG. 19 is a print-out of data obtained by processing data of the PCR in steps 1), 2), 3), 4) and 5). Concerning $75^{th}$ amplification products of the 1 copy and 10 copies, data were processed in steps 1) 2) and 3) of this Example. The nucleic acid melting curves so obtained are shown in FIG. 20. Those curves were differentiated in step 4), and points of inflection (Tm values) were determined in step 5) and 6). The differentiated curves with the points of inflection are ilustrated in FIG. 21. It was ascertained from FIG. 21 that the amplification products of the 1 copy and 10 copies were different products as their Tm values were different from each other.

What is claimed is:

1. A method for analyzing data obtained by a method for analyzing or determining a polymorphism or a mutation in a target nucleic acid or gene, which comprises:

correcting a fluorescence intensity of a reaction system, in which said target nucleic acid or gene has been hybridized with a nucleic acid probe labeled with a fluorescent dye, in accordance with a fluorescence intensity of said reaction system before said hybridization; wherein the method for analyzing or determining polymorphism or mutation of a target nucleic acid or gene comprises:

hybridizing the nucleic acid probe to said target nucleic acid or gene, wherein only said nucleic acid probe is provided for one type of target nucleic acid, and measuring a change in fluorescence;

wherein said probe is labeled at an end portion thereof with said fluorescent dye, and said probe has a base sequence designed such that, when said probe is hybridized with said target nucleic acid, at least one guanine base exists in a base sequence of said target nucleic acid at a position 1 to 3 bases from an end base portion where said probe and said target nucleic acid are hybridized with each other;

whereby said fluorescent dye is reduced in fluorescence emission when said probe is hybridized with said target nucleic acid.

2. The method according to claim 1, wherein said probe has G or C as a 3' end base and is labeled at said 3' end thereof with said fluorescent dye.

3. The method according to claim 1 wherein the nucleic acid probe has G or C as a 5' end base and is labeled at said 5' end thereof with said fluorescent dye.

4. The method according to claim 1, wherein a hydroxyl group of a 2' or 3' carbon of a ribose or a 3' carbon of a deoxyribose at 3' end of said probe has been phosphorylated.

5. The method according to claim 1, wherein an oligoribonucleotide of said probe is a chemically-modified nucleic acid.

6. The method according to claim 1, wherein an oligonucleotide of said probe is a chimeric oligonucleotide comprising a ribonucleotide and a deoxyribonucleotide.

7. The method according to claim 6, wherein said ribonucleotide is a 2'-O-methyloligoribonucleotide.

8. A system for analyzing or determining a polymorphism or a mutation in a target nucleic acid or gene, comprising a means for analyzing data as defined in claim 1.

9. A computer-readable, recording medium comprising a recorded program to perform the correcting as defined in claim 1.

10. A method for analyzing data obtained by a method for determining a concentration of a target nucleic acid with a nucleic acid probe labeled with a fluorescent dye, comprising correcting an intensity value of fluorescence of a reaction system, said intensity value being available after said target nucleic acid has hybridized to said nucleic acid probe labeled with said fluorescent dye, in accordance with an intensity value of fluorescence of said reaction system available after a probe-nucleic acid hybrid complex so formed has dissociated;

wherein the method for determining a concentration of the target nucleic acid comprises:

providing, as said probe, a nucleic acid probe that reduces fluorescence emission from said fluorescent dye when hybridized with said target nucleic acid;

hybridizing said probe to said target nucleic acid, wherein only said nucleic acid probe is provided for one type of target nucleic acid; and measuring a decrease in fluorescence emission from said fluorescent dye after said hybridization relative to fluorescence emission from said fluorescent dye before said hybridization.

11. The method according to claim 10, wherein said probe has G or C as a 3' end base and is labeled at said 3' end thereof with said fluorescent dye.

12. The method according to claim 10, wherein the nucleic acid probe has G or C as a 5' end base and is labeled at said 5' end thereof with said fluorescent dye.

13. The method according to claim 10, wherein a hydroxyl group of a 2' or 3' carbon of a ribose or a 3' carbon of a deoxyribose at 3' end of said probe has been phosphorylated.

14. The method according to claim 10, wherein an oligoribonucleotide of said probe is a chemically-modified nucleic acid.

15. The method according to claim 10, wherein an oligonucleotide of said probe is a chimeric oligonucleotide comprising a ribonucleotide and a deoxyribonucleotide.

16. The method according to claim 15, wherein said ribonucleotide is a 2'-O-methyloligoribonucleotide.

17. A system for analyzing or determining a polymorphism or a mutation in a target nucleic acid or gene, comprising a means for analyzing data as defined in claim 10.

18. A computer-readable, recording medium comprising a recorded program to perform the correcting as defined in claim 10.

19. A method for analyzing data obtained by a real-time quantitative PCR method wherein said method comprises conducting a real-time quantitative PCR reaction with a nucleic acid probe;

measuring an intensity of fluorescence of a reaction system in which at a time of a nucleic acid extending reaction, said probe has been degraded by a polymerase or by a nucleic acid denaturing reaction in the reaction; and also measuring an intensity of fluorescence of said reaction in which a target nucleic acid or amplified target nucleic acid has hybridized with said nucleic acid probe; and then calculating a decrease of said latter intensity of fluorescence from said former intensity of fluorescence as a correction processing step, correcting an intensity value of fluorescence of a reaction system, said intensity being available in each cycle after said amplified nucleic acid has conjugated to said fluorescent dye or after said amplified nucleic acid has hybridized to said nucleic acid probe labeled with said fluorescent dye, in accordance with an intensity value of fluorescence of said reaction system available after a nucleic acid-fluorescent dye conjugate or probe-nucleic acid hybrid complex so formed has dissociated in said cycle;

wherein said probe is labeled with a fluorescent dye, wherein:

said probe is labeled at an end portion thereof with said fluorescent dye, and said probe has a base sequence designed such that, when said probe is hybridized with said target nucleic acid, at least one guanine base exists in a base sequence of said target nucleic acid at a position 1 to 3 bases apart from an end base portion where said probe and said target nucleic acid are hybridized with each other;

whereby said fluorescent dye is reduced in fluorescence emission when said probe is hybridized with said target nucleic acid;

wherein said correction-processing step is performed in accordance with the following formula (1) or formula (2):

$$f_n = f_{hyb,n}/f_{den,n} \quad (1)$$

$$f_n = f_{den,n}/f_{hyb,n} \quad (2)$$

wherein $f_n$: correction-processed value in an $n^{th}$ cycle as calculated in accordance with the formula (1) or formula (2), $f_{hyb,n}$: intensity value of fluorescence of the reaction system available after said amplified nucleic acid has conjugated to said fluorescent dye or said amplified nucleic acid has hybridized to said nucleic acid probe labeled with said fluorescent dye in said $n^{th}$ cycle, and $f_{den,n}$: intensify value of fluorescence of the reaction system available after said nucleic acid-fluorescent dye conjugate has dissociated in said $n^{th}$ cycle or said probe-nucleic acid hybrid complex has dissociated in said $n^{th}$ cycle.

20. The method according to claim 19, which further comprises:

introducing correction-processed values, which have been calculated in accordance with the formula (1) or formula (2) in individual cycles, into the following formula (3) or (4) to calculate rates or percentages of changes in fluorescence between samples in said individual cycles:

$$F_n = f_n/f_a \quad (3)$$

$$F_a = f_a/f_n \quad (4)$$

wherein $F_n$: rate or percentage of a change in fluorescence in an $n^{th}$ cycle as calculated in accordance with the formula (3) or formula (4), $f_n$: correction-processed value calculated in said $n^{th}$ cycle as calculated in accordance with the formula (1) or formula (2), and $f_a$: correction-processed value calculated in a given cycle before a change in $f_n$ is observed as calculated in accordance with the formula (1) or formula (2); and comparing said rates or percentages of changes in fluorescence.

21. The method according to claim 20, which further comprises the following processing steps:

1) processing in accordance with the following formula (5), (6) or (7) using data of rates or percentages of charges in fluorescence as calculated in accordance with said formula (3) or (4):

$$\log_b(F_n), \ln(F_n) \quad (5)$$

$$\log_b\{(1-F_n) \times A\}, \ln\{(1-F_n) \times A\} \quad (6)$$

$$\log_b\{(F_n-1) \times A\}, \ln\{F_n-1) \times A\} \quad (7)$$

wherein

A,b: desired numerical values, and $F_n$: rate or percentage of a change in fluorescence in an $n^{th}$ cycle as calculated in accordance with the formula (3) or formula (4), 2) determining a cycle (Ct value) in which the processed value of the processing step 1) has reached a threshold, 3) calculating a relational expression between the Ct value in step 2) of a nucleic acid sample of a known concentration and the number of copies of said target nucleic acid at the time of initiation of the PCR reaction, and 4) determining the number of copies the target nucleic in the PCR reaction.

22. The method according to claim 19, which further comprises the following steps:
- gradually heating a PCR-amplified nucleic acid from a low temperature until complete denaturation of said nucleic acid;
- measuring an intensity of fluorescence at predetermined time intervals during said heating step;
- displaying results of said measurement as a function of time on a display such that a melting curve of said nucleic acid is drawn on said display;
- differentiating said melting curve to obtain differentiated values (−dF/dT, F: intensity of fluorescence, T: time);
- displaying said differentiated values as derivatives on said display; and
- determining a point of inflection from said derivatives.

23. The method according to claim 19, wherein said probe has G or C as a 3' end base and is labeled at said 3' end thereof with said fluorescent dye.

24. The method according to claim 19, wherein the nucleic acid probe has G or C as a 5' end base and is labeled at said 5' end thereof with said fluorescent dye.

25. The method according to claim 19, wherein a hydroxyl group of a 2' or 3' carbon of a ribose or a 3' carbon of a deoxyribose at 3' end of said probe has been phosphorylated.

26. The method according to claim 19, wherein an oligoribonucleotide of said probe is a chemically-modified nucleic acid.

27. The method according to claim 19, wherein an oligonucleotide of said probe is a chimeric oligonucleotide comprising a ribonucleotide and a deoxyribonucleotide.

28. The method according to claim 27, wherein said ribonucleotide is a 2'-O-methyloligoribonucleotide.

29. A system for analyzing or determining a polymorphism or a mutation in a target nucleic acid or gene, comprising a means for analyzing data as defined in claim 19.

30. A computer-readable, recording medium comprising a recorded program to perform the correcting as defined in claim 19.

31. A method for analyzing a melting curve of a target nucleic acid, which comprises:
- performing PCR on said target nucleic acid with a nucleic acid probe which is labeled with a fluorescent dye,
- wherein said probe is labeled at an end portion thereof with said fluorescent dye, and
- said probe has a base sequence designed such that, when said probe is hybridized with said target nucleic acid, at least one guanine base exists in a base sequence of said target nucleic acid at a position 1 to 3 bases apart from an end base portion where said probe and said target nucleic acid are hybridized with each other;
- whereby said fluorescent dye is reduced in fluorescence emission when said probe is hybridized with said target nucleic acid, wherein only said nucleic acid probe is provided for one type of target nucleic acid; and
- analyzing the melting curve of said target nucleic acid to determine a Tm value of each amplified nucleic acid.

32. The method according to claim 31, wherein said probe has G or C as a 3' end base and is labeled at said 3' end thereof with said fluorescent dye.

33. The method according to claim 31, wherein the nucleic acid probe has G or C as a 5' end base and is labeled at said 5' end thereof with said fluorescent dye.

34. The method according to claim 31, wherein a hydroxyl group of a 2' or 3' carbon of a ribose or a 3' carbon of a deoxyribose at 3' end of said probe has been phosphorylated.

35. The method according to claim 31, wherein an oligoribonucleotide of said probe is a chemically-modified nucleic acid.

36. The method according to claim 31, wherein an oligonucleotide of said probe is a chimeric oligonucleotide comprising a ribonucleotide and a deoxyribonucleotide.

37. The method according to claim 36, wherein said ribonucleotide is a 2'-O-methyloligoribonucleotide.

38. A system for analyzing or determining a polymorphism or a mutation in a target nucleic acid or gene, comprising a means for analyzing data as defined in claim 31.

39. A computer-readable, recording medium comprising a recorded program to perform the correcting as defined in claim 31.

40. A method for analyzing a melting curve of a target nucleic acid, which comprises:
- performing PCR on said target nucleic acid by using a nucleic acid probe as a primer; and
- analyzing said melting curve of said target nucleic acid to determine a Tm value of each amplified nucleic acid;
- wherein said nucleic acid probe said probe is labeled with a fluorescent dye, wherein:
  - said probe is labeled at the 5' end thereof with said fluorescent dye, and said probe has a base sequence designed such that, when said probe is hybridized with said target nucleic acid, at least one G (guanine) base exists in a base sequence of said target nucleic acid at a position 1 to 3 bases apart from an end base portion where said probe and said target nucleic acid are hybridized with each other;
  - whereby said fluorescent dye is reduced in fluorescence emission when said probe is hybridized with said target nucleic acid.

41. The method according to claim 40, wherein said probe has G or C as a 3' end base and is labeled at said 3' end thereof with said fluorescent dye.

42. The method according to claim 40, wherein the nucleic acid probe has G or C as a 5' end base and is labeled at said 5' end thereof with said fluorescent dye.

43. The method according to claim 40, wherein a hydroxyl group of a 2' or 3' carbon of a ribose or a 3' carbon of a deoxyribose at 3' end of said probe has been phosphorylated.

44. The method according to claim 40, wherein an oligoribonucleotide of said probe is a chemically-modified nucleic acid.

45. The method according to claim 40, wherein an oligonucleotide of said probe is a chimeric oligonucleotide comprising a ribonucleotide and a deoxyribonucleotide.

46. The method according to claim 45, wherein said ribonucleotide is a 2'-O-methyloligoribonucleotide.

47. A system for analyzing or determining a polymorphism or a mutation in a target nucleic acid or gene, comprising a means for analyzing data as defined in claim 40.

48. A computer-readable, recording medium comprising a recorded program to perform the correcting as defined in claim 40.

* * * * *